(12) United States Patent
Filpula et al.

(10) Patent No.: US 7,807,436 B2
(45) Date of Patent: Oct. 5, 2010

(54) RECOMBINANT HOST FOR PRODUCING L-ASPARAGINASE II

(75) Inventors: David Ray Filpula, Piscataway, NJ (US); Maoliang Wang, East Brunswick, NJ (US)

(73) Assignee: Defiante Farmaceutica, S.A., Funchal-Madeira (PT)

( * ) Notice: Subject to any disclaimer, the term of this patent is extended or adjusted under 35 U.S.C. 154(b) by 2 days.

(21) Appl. No.: 11/759,988

(22) Filed: Jun. 8, 2007

(65) Prior Publication Data

US 2008/0063632 A1 Mar. 13, 2008

Related U.S. Application Data

(60) Provisional application No. 60/817,817, filed on Jun. 30, 2006.

(51) Int. Cl.
| | |
|---|---|
| C12P 21/00 | (2006.01) |
| C12N 15/00 | (2006.01) |
| C12N 1/21 | (2006.01) |
| C07H 21/00 | (2006.01) |
| C12N 9/82 | (2006.01) |
| C12Q 1/34 | (2006.01) |
| C07K 14/00 | (2006.01) |

(52) U.S. Cl. ............... 435/229; 435/252.33; 435/320.1; 435/69.1; 435/18; 536/23.2; 530/350

(58) Field of Classification Search ........................ None
See application file for complete search history.

(56) References Cited

U.S. PATENT DOCUMENTS

| | | | |
|---|---|---|---|
| 5,122,614 | A | 6/1992 | Zalipsky |
| 5,324,844 | A | 6/1994 | Zalipsky |
| 5,612,460 | A | 3/1997 | Zalipsky |
| 5,643,575 | A | 7/1997 | Martinez et al. |
| 5,808,096 | A | 9/1998 | Zalipsky |
| 5,919,455 | A | 7/1999 | Greenwald et al. |
| 5,965,119 | A | 10/1999 | Greenwald et al. |
| 6,113,906 | A | 9/2000 | Greenwald et al. |
| 6,180,095 | B1 | 1/2001 | Greenwald et al. |
| 6,303,569 | B1 | 10/2001 | Greenwald et al. |
| 7,087,229 | B2 | 8/2006 | Zhao et al. |
| 7,122,189 | B2 | 10/2006 | Zhao et al. |
| 7,413,739 | B2 | 8/2008 | Hubbell et al. |

OTHER PUBLICATIONS

Wang et al. (2001) Applied Biochemistry and Biotechnology, vol. 95 (2), pp. 93-101.*
Khushoo et al., Protein Expression and Purification 38:29-36, 2004.*
Yang et al., GenBank accession No. ABB63129, Nov. 2005.*
Maita et al., The primary structure of L-asparaginase from *Escherichia coli*, Hoppe Seyler's Z. Physiol. Chem., 1980, vol. 361(2), pp. 105-117.
Maita et al., Amino acid aequence of L-Asparaginase from *Escherichia coli*, J. Biochem, 1974, vol. 76, pp. 1351-1354.
Jennings et al., Analysis of *Escherichia coli* gene encoding L-asparaginase II, ansB, and its . . . , J. Bacteriol, Mar. 1990, vol. 172, pp. 1491-1498.
Guo et al., Comparison of antitumor effect of recombinant L-asparaginase with wild type one in vitro and in vivo, Acta Pharmacol Sin, 2002, vol. 23(10), pp. 946-951.
International Search Report and Written Opinion dated Aug. 8, 2008 issued in PCT/US/07/70706.
Supplementary European Search Report issued in EP 07840229 and dated Mar. 11, 2010.
Toncic et al., "An automated assay for the determination of asparaginase activity", Journal of Biological Standardization, 10:297-302, 1982.
Tsurusawa et al., "L-Asparagine depletion levels and L-asparaginase activity in plasma of children with acute lymphoblastic leukemia under asparaginase treatment", Cancer Chemotherapy and Pharmacology, 53: 204-208, 2004.
Pinheiro Vieira et al: Serum asparaginase activities and asparagine concentrations in the cerebrospinal fluid after a single infusion of 2,500 IU/m(2) PEG asparaginase in children with ALL treated according to protocol COALL-06-97", Pediatric Blood & Cancer, 46: 18-25, 2006.

* cited by examiner

*Primary Examiner*—Delia M Ramirez
(74) *Attorney, Agent, or Firm*—Lucas & Mercanti, LLP

(57) ABSTRACT

The invention provides a recombinant *Escherichia coli* host cell for producing an *Escherichia coli*-asparaginase II enzyme. The host cell includes an *Escherichia coli* chromosome and at least one copy of a recombinant extrachromosomal vector, wherein the recombinant extrachromosomal vector encodes the L-asparaginase II enzyme, wherein the host cell chromosome also encodes the same L-asparaginase II enzyme, and wherein the host chromosome does not encode any other isoform of L-asparaginase II.

15 Claims, 1 Drawing Sheet

RECOMBINANT HOST FOR PRODUCING L-ASPARAGINASE II

The present application claims the benefit of provisional U.S. patent application Ser. No. 60/817,817, filed on Jun. 30, 2006, the contents of which are incorporated by reference herein in their entirety.

FIELD OF THE INVENTION

The present invention relates to novel vectors, host cells and methods of producing a specific recombinant *E. coli* L-asparaginase II enzyme of uniform purity.

DESCRIPTION OF THE RELATED ART

L-asparaginase is an enzyme that hydrolyzes the amino acid L-asparagine to L-aspartate and ammonia, i.e., it is a deaminating enzyme. *E. coli* contain two asparaginase isoenzymes: L-asparaginase I and L-asparaginase II. L-asparaginase I is located in the cytosol and has a low affinity for asparagine. L-asparaginase II is located in the periplasm and has a high affinity for L-asparagine.

L-asparaginase II is useful in treating tumors or cancers that are dependent upon L-asparagine for protein synthesis by removing extracellular asparagine. It is particularly useful in treating leukemias, such as acute lymphoblastic leukemia. L-asparaginase is typically used in combination with other anti-tumor or anticancer therapies, although it can be employed alone in certain clinical situations. L-asparaginase was originally purified from several organisms, including *Escherichia coli* ("*E. coli*") and *Erwinia carotovora*. Among mammals, L-asparaginase II is found in more than trace amounts only in Guinea pigs (superfamily Cavioidea) and in certain New World monkeys.

*E. coli* L-asparaginase II is a tetramer of identical subunits exhibiting excellent $k_{cat}$ and $K_m$. *E. coli* L-asparaginase II (also art-known as L-asparagine amidohydrolase, type EC-2, EC 3.5.1.1) is commercially available as Elspar® (Merck & Co., Inc.) and is also available from Kyowa Hakko Kogyo Co., Ltd.

L-asparaginase II, by itself, suffers from the usual disadvantages of protein therapeutics, such as the high rate of clearance of a protein foreign to the patient, and the potential for inducing an immune response in a patient treated with this enzyme. In order to address these shortcomings, a polyethylene glycol-conjugated derivative of L-asparaginase II has been developed and is marketed as pegaspargase or Oncaspar® by Enzon Pharmaceuticals, Inc. Pegaspargase is produced using L-asparaginase II extracted from *E. coli*, as supplied by Merck. Pegaspargase (also known as monomethoxy polyethylene glycol succinimidyl L-asparaginase) has the advantages of being substantially non-antigenic, and of exhibiting a reduced rate of clearance from the circulation.

However, despite these successes, it would be still more efficient and economical if *E. coli* L-asparaginase II protein could be produced by a recombinant host cell employing a suitable extrachromosomal expression vector, e.g., such as a plasmid. Such expression vectors can be engineered for more efficient production of the protein than is available with production from a native *E. coli* strain. Despite the potential advantages of such recombinant production, it is believed that heretofore there has been no accurate published polypeptide sequence for the commercial L-asparaginase II enzyme, and no published nucleic acid sequence for polynucleotides encoding that enzyme. For example, an L-asparaginase II peptide sequence was previously reported by Maita et al. 1980, *Hoppe Seyler's Z. Physiol. Chem.* 361(2), 105-117, and Maita et al., 1974, *Biochem.* 76, 1351-1354 [Tokyo]. However, as discussed hereinbelow, this early work suffered from numerous sequencing errors.

Another potential obstacle to plasmid expression of the L-asparaginase II enzyme subunit is the presence of the gene encoding an L-asparaginase II subunit that is native to the chromosome of potential *E. coli* strains that might be employed as host cells. Thus, there is a concern that L-asparaginase II harvested from an *E. coli* host cell carrying an extrachromosomal expression vector could include subunits representing more than one isoform of L-asparaginase. Given the need to have a well characterized enzyme product, for both clinical and regulatory purposes, this possibility has heretofore represented a serious technical challenge to improving on the efficiency of the production of *E. coli* L-asparaginase II protein.

SUMMARY OF THE INVENTION

The present invention fills the above-mentioned need for *E. coli* L-asparaginase II that is produced efficiently and economically in recombinant form, while providing an enzyme product having the same peptide structure as *E. coli* L-asparaginase II protein, marketed as Oncaspar®, that is also free of detectable amounts of alternative L-asparaginase II isoforms.

Thus, the invention provides an E. coli host cell comprising an *E. coli* chromosome and at least one copy of a recombinant extrachromosomal vector, wherein the extrachromosomal vector encodes a subunit of the L-asparaginase II protein, wherein the *E. coli* host cell chromosome encodes the same subunit of the L-asparaginase protein, and wherein the *E. coli* host chromosome does not encode any other isoform of L-asparaginase II. The extrachromosomal vector is preferably a plasmid suitable for replication and expression in *E. coli*.

Preferably, the expressed L-asparaginase protein comprises four subunits that have a polypeptide sequence according to SEQ ID NO:1, that corresponds to the sequence of the subunits of the L-asparaginase II enzyme used in manufacturing Oncaspar®, and the plasmid vector comprises a nucleic acid molecule encoding a subunit of the L-asparaginase protein, that is operatively connected to a suitable promoter. The promoter is any suitable promoter, but is optionally selected from the group consisting of T7, araB, trp, tac, lac, $\lambda P_L$, $\lambda P_R$, aroH and phoA promoters. The plasmid vector optionally includes additional vector elements, as may be needed for efficient expression and/or product purification, that are operably connected to the L-asparaginase open reading frame and/or the promoter. These vector elements include, for example, a compatible operator sequence, ribosome binding site, transcriptional terminator, signal sequence, drug resistance marker, and origin of replication. A plasmid borne copy of the relevant repressor genie, e.g. lacI, may also be present.

Preferably, the plasmid DNA molecule encoding the subunit of the L-asparaginase II protein comprises SEQ ID NO: 2, and the chromosomal DNA molecule encoding the L-asparaginase II protein comprises SEQ ID NO: 3.

DETAILED DESCRIPTION OF THE INVENTION

Figure 1:
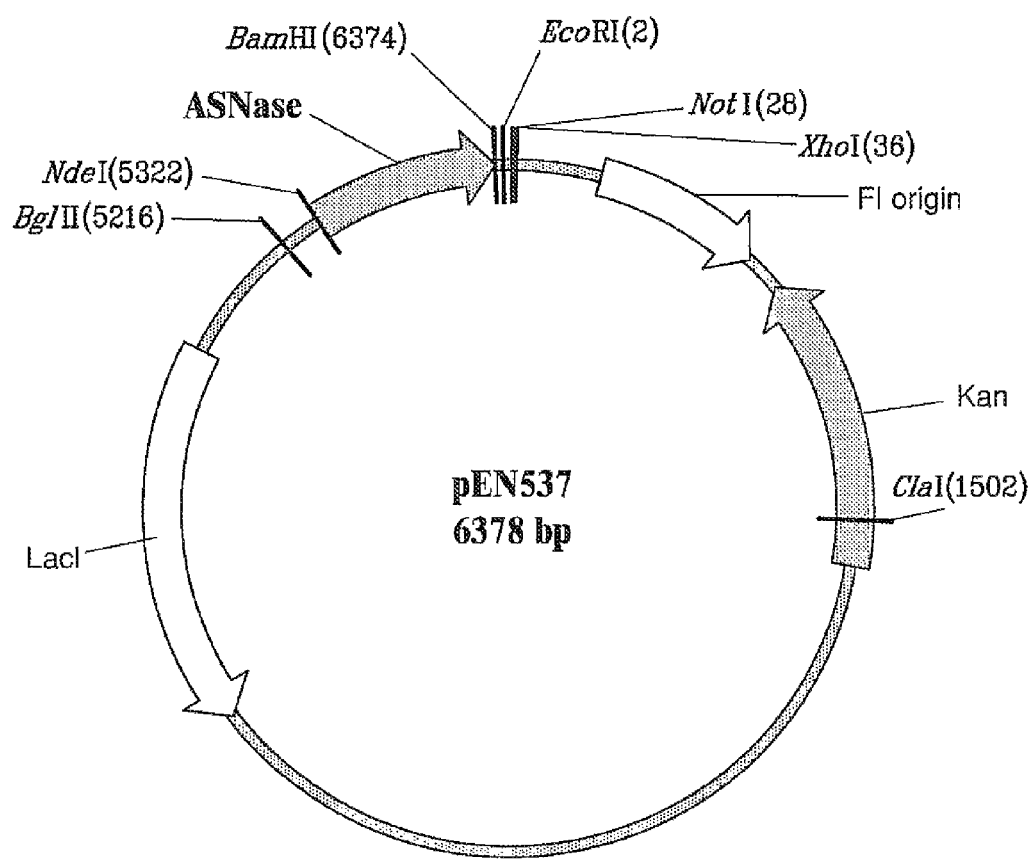
FIG. 1 illustrates a map of the pEN537 plasmid vector.

Accordingly, in order to provide the desired improvements in the production of the L-asparaginase II corresponding to Oncaspar® and Kyowa Hakko L-asparaginase, it is necessary to obtain a vector encoding the enzyme, and also to provide a host cell that will only express a single isoform of L-asparaginase II. Thus, L-asparaginase II enzyme from Merck & Co., Inc., as well as L-asparaginase II enzyme obtained from Kyowa Hakko Kogyo Co., Ltd. were sequenced, and the resulting sequences were compared to that of the L-asparaginase II enzyme obtained from *E. coli* K-12, as reported by Jennings et al., 1990 *J Bacteriol* 172: 1491-1498, incorporated by reference herein. The K12 L-asparaginase II enzyme is encoded by the ansB gene (GeneBank No. M34277, incorporated by reference herein).

As noted above, the artisan will appreciate that L-asparaginase II enzyme comprises four identical subunits. Thus, reference to a gene or DNA molecule encoding the enzyme, and the enzyme protein sequence, refers to the gene encoding one of these identical subunits.

The peptide sequencing was conducted by art-standard methods, as summarized by Example 1, hereinbelow. The protein sequences of subunits of both the Merck & Co., Inc., and the Kyowa Hakko Kogyo Co., Ltd. were surprisingly found to be identical (see SEQ ID NO: 1). With this data, it can now be appreciated that earlier reports of the sequence of the Merck L-asparaginase by Maita et al. 1980 *Hoppe Seyler's Z. Physiol. Chem.* 361(2), 105-117, and Maita et al., 1974, *J. Biochem.* 76, 1351-1354 [Tokyo] actually contained numerous errors.

The obtained sequences were also compared to the subunit structure of the K12 L-asparaginase II enzyme. It was found that the K12 L-asparaginase II enzyme subunit differs from the Merck & Co., Inc. L-asparaginase II enzyme subunit at four specific residue positions. Relative to the Merck L-asparaginase II enzyme, the K12 enzyme subunit has $Val_{27}$ in place of $Ala_{27}$, $Asn_{64}$ in place of $Asp_{64}$, $Ser_{252}$ in place of $Thr_{252}$ and $Thr_{263}$ in place of $Asn_{263}$.

As noted supra, it is preferred that the chromosome of the *E. coli* host cell does not express a different isoform of L-asparaginase II than is expressed by the extrachromosomal vector, i.e., by a plasmid. This desirable result can be achieved by one of several alternative strategies. For example, any L-asparaginase II gene present on the *E. coli* host chromosome could be fully or partially deleted or knocked out. Alternatively, the expression of any alternative L-asparaginase II gene present on the host chromosome could be suppressed by intrinsic regulatory properties of the natural promoter with one that fails to allow expression under the same culture conditions that favor the expression of the isoform of L-asparaginase II encoded by the extrachromosomal vector. However, it is preferable to have the chromosomal and extrachromosomal L-asparaginase II genes express the same isoform of the L-asparaginase II enzyme.

To this end, the subunits of the L-asparaginase II enzyme produced by several available *E. coli* strains were sequenced and compared to the commercial enzyme products. It was unexpectedly discovered that the *E. coli* BLR (DE3) strain [obtained from Novagen Corporation; Cat. No. 69208-3] produces a chromosomally encoded L-asparaginase II enzyme identical in structure to the commercially available enzymes, whereas the E. coli GX1210 and *E. coli* GX6712 strains that were also tested were found to produce different isoforms of L-asparaginase II enzyme.

With the identification of a preferred *E. coli* host, an extrachromosomal expression vector, i.e., a vector which exists as an extrachromosomal entity, the replication of which is independent of chromosomal replication, can be constructed. Extrachromosomal vectors suitable for use in E. coli include, for example, pUC or pBR322 derived plasmids. These include plasmids such as pET and pBAD, as well as a variety of plasmids having expression elements from T7, araBAD, phoA, trc, or, $O_L$, $O_R$, $P_L$, $P_R$.

In the vector, the nucleic acid sequence encoding the L-asparaginase II enzyme subunit is operably connected to a suitable promoter sequence. Suitable promoters include, e.g., the T7, araBAD, phoA, trc, $O_L$, $O_R$, $P_L$ and $P_R$ promoters. Preferably, the promoter is a T7 viral promoter.

Suitable inducer elements include, for example, arabinose, lactose, or heat induction, phosphate limitation, tryptophan limitation, to name but a few. Preferably, the inducer element is a Lac operon, which is inducible by isopropyl thiogalactoside ("IPTG").

A suitable signal sequence (signal peptide) may be derived from pelB, fd pIII, or ompA. Preferably the signal peptide is derived from ansB.

Suitable antibiotic selection markers are well known to the art and include, for example, those that confer ampicillin, kanamycin, chloramphenicol, rifampicin, or tetracycline resistance, among others.

Suitable origin of replication sequences include those found in the following Plasmids: pUC19, pACY177, pUB110, pE194, pAMB1, pIJ702, pBR322, pBR327, and pSC101.

Suitable termination sequences include, for example, phage fd major terminator, TF, and rrnB.

Generally plasmids are preferred for use in *E. coli*. Conventional plasmid vectors are double-stranded circular DNA molecules preferably engineered with enzyme recognition sites suitable for inserting exogenous DNA sequences, an antibiotic selectable gene, an origin of replication for autonomous propagation in the host cell, and a gene for the discrimination or selection of clones that contain recombinant insert DNA. Available plasmid vectors include, for example, pET3, pET9, pET11 and the extended pET series (cataloged by Novagen Corporation), pBAD, trc phoA, trp, and $O_{L/R}/P_{L/R}$ plasmids.

As exemplified hereinbelow, a plasmid of the pET expression system, such as pET 27b+ is preferred. In order to provide efficient and controlled expression of the enzyme, the expression vector also includes a promoter, an operator, ribosome binding site, signal sequence, transcriptional terminator, origin of replication, a regulated copy of the repressor gene (e.g., lacI)

The host *E. coli* strain will have compatible regulatory elements in its chromosome. For example the gene for T7 RNA polymerase under the control of the lacUV5 promoter is present in BLR (DES) cells. This strain is a lysogen of bacteriophage DE3. Addition of IPTG to the culture of BLR (DE3) induces T7 RNA polymerase, which in turn transcribes the target gene on the pET plasmid. BLR(DE3) is also recA which may provide further stability of genes on extrachromosomal plasmids.

In order to obtain a nucleic acid molecule encoding the Merck and Kyowa Hakko Kogyo Co., Ltd. enzyme, an available L-asparaginase II can be modified by suitable methods. The 326 mature amino acid sequence L-asparaginase II subunit of *E. coli* K-12 ansB is encoded in a 978 base pair segment as reported by Jennings M P and Beacham I R (1990 J Bacteriol 172: 1491-1498; GeneBank No. M34277). The ansB gene, which includes a 22 amino acid signal peptide preceding the mature protein, was cloned from another E. coli K-12 strain (GX1210; obtained, from Genex Corporation) by conventional polymerase chain reaction (PCR) methods. The ansB gene encoding *E. coli* K-12 ansB L-asparaginase II sub-unit was adapted by site-directed mutagenesis (e.g., with the Amersham Sculptor method) to express L-asparaginase II with the residue substitutions discussed supra, to make the following base substitutions. T to C at base 530; A to G at base 640; T to A at base 1205 and C to A at base 1239. Numbering is based on that given by GeneBank No. M34277, incorporated by reference herein. The resulting codon changes [GTG to GC<u>G</u>; AAT to GAT; TCT to ACT and ACC to AAC at the corresponding positions] converted the ansB gene to a modified gene (hereinafter ansB*; SEQ ID NO: 2) that expresses an L-asparaginase II enzyme subunit identical to that obtained from Merck & Co., Inc. and Kyowa Hakko Kogyo Co., Ltd.

The ansB* gene can be inserted into any extrachromosomal vector suitable for efficient protein expression in *E. coli*, as discussed above. In particular, the ansB* gene was inserted into plasmid pET-27b+ (Novagen Corporation) and introduced into *E. coli* strain BLR (DE3) by electroporation, as described in detail by the examples provided hereinbelow, to provide an *E. coli* carrying the ansB* plasmid and expressing L-asparaginase II subunit as a uniform isoform matching the Merck L-asparaginase II.

Preferably, the clone identified by the examples as strain E-N538 (deposited as ATCC Number PTA 7490) is employed and cultured employing any art-known method suitable for E. coli. Suitable culture systems include batch, fed batch and continuous culture methods. Culture medium are selected from art-known medium optimized for *E. coli*. Once the culture reaches a sufficient density, ranging from about 20 $OD_{660}$ to about 200 $OD_{660}$, an appropriate inducer, such as IPTG, is added to the culture medium. After a sufficient period of time, ranging from about 0.5 hours to about 20 hours, the produced L-asparaginase II is purified by standard methods from the culture medium and/or from cell mass harvested from the culture.

The cell mass is harvested by centrifugation and/or filtration, and lysed by any art-known method. Lysis of the cell bodies can be accomplished by methods including enzymatic cell wall lysis followed by osmotic lysis, freeze thaw, sonication, mechanical disruption (e.g., microfluidization), use of lysing agents and the like, followed by filtration and/or centrifugation to separate the disrupted cell mass from the soluble protein contents. Several cycles of lysis, washing and separation can be employed to optimize recovery.

The enzyme can then be recovered and purified from supernatant and/or culture medium by well-known purification methods including ammonium sulfate precipitation, acid extraction, chromatofocusing, anion or cationic exchange chromatography, phosphocellulose chromatography, hydrophobic-interaction chromatography, affinity chromatography, hydroxylapatite chromatography, FPLC® (fast protein liquid chromatography), high performance liquid chromatography, and the like.

Several parameters of the fermentation process may be adjusted to optimize the asparaginase expression or to control the extent of leakage of the protein from the periplasm into the growth medium. These variables include the medium constituents (e.g., carbon and nitrogen source and added amino acids or other nutrients), temperature, pH, inducer concentration, and duration of expression. The total *E. coli* genetic lineage (genotype) may also affect expression and product leakage. It may be desirable to harvest the asparaginase product from cells (periplasm) only, or from medium only, or from the total fermenter contents depending on the outcome of the protein expression and leakage from the host cells.

Polymer-L-Asparaginase Conjugates

A preferred utility for the L-asparaginase II enzyme prepared according to the invention is in the form of a polymer conjugated enzyme. The L-asparaginase-polymer conjugates of the present invention generally correspond to formula (I):

wherein (ASN) represents the L-asparaginase or a derivative or fragment thereof;

NH— is an amino group of an amino acid found on the ASN, derivative or fragment thereof for attachment to the polymer;

z is a positive integer, preferably from about 1 to about 80; and

R is a substantially non-antigenic polymer residue that is attached to the ASN in a releasable or non-releasable form.

The non-antigenic polymer residue portion of the conjugate (R) can be selected from among a non-limiting list of polymer based systems such as:

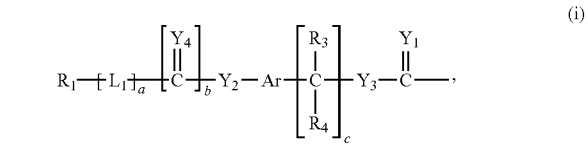

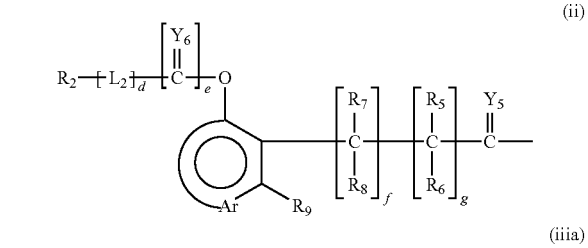

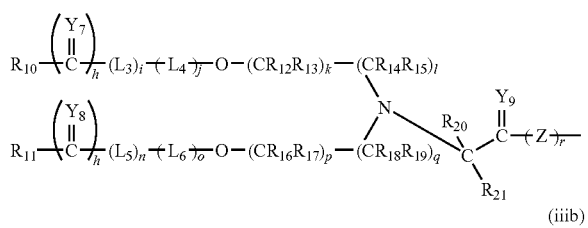

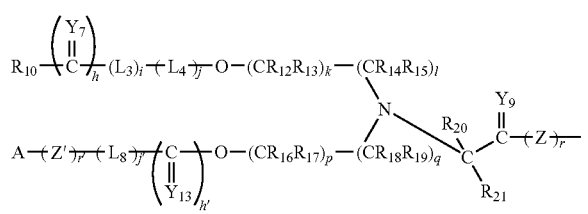

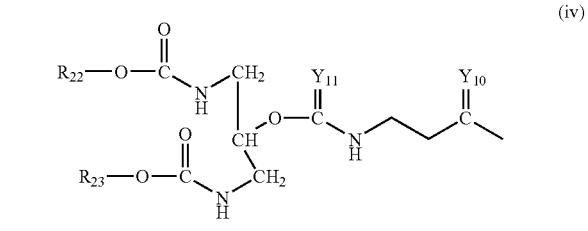

-continued

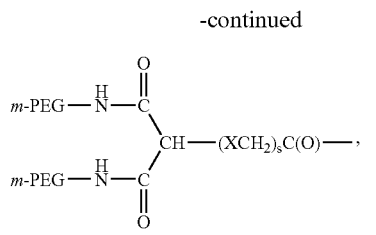
(v)

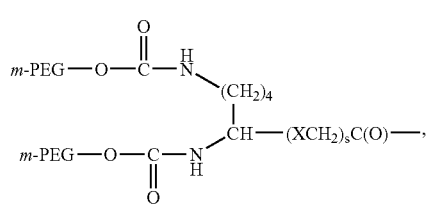
(vi)

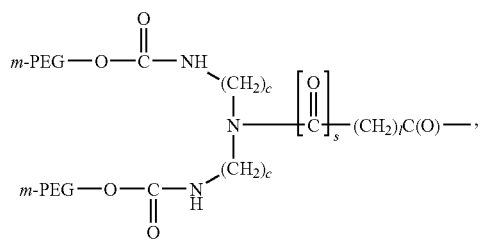
(vii)

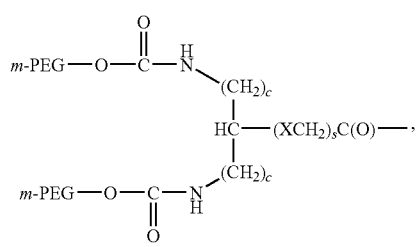
(viii)

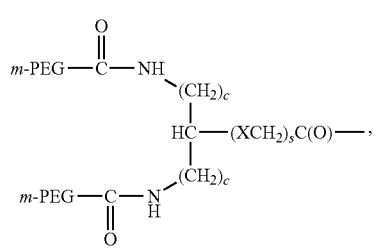
(ix)

-continued

(x)

and

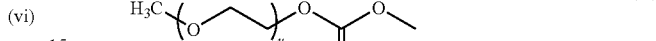
(xi)

wherein:

$R_{1-2}$, $R_{10-11}$, and $R_{22-23}$ may be the same or different and are independently selected non-antigenic polymer residues;

$R_{3-9}$, $R_{12-21}$ and $R_{24}$ (see below) are the same or different and are each independently selected from among hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxys;

Ar is an aromatic moiety which forms a multi-substituted aromatic hydrocarbon or a multi-substituted heteroaromatic group;

$Y_{1-11}$ and $Y_{13}$ may be the same or different and are independently selected from O, S and $NR_{24}$;

A is selected from among hydrogen, alkyl groups, targeting moieties, leaving groups, functional groups, diagnostic agents, and biologically active moieties;

X is O, NQ, S, SO or $SO_2$; where Q is H, $C_{1-8}$ alkyl, $C_{1-8}$ branched alkyl, $C_{1-8}$ substituted alkyl, aryl or aralkyl;

Z is selected from among moieties actively transported into a target cell, hydrophobic moieties, bifunctional linking moieties and combinations thereof;

$L_{1-6}$ and $L_8$ may be the same or different and are independently selected bifunctional linker groups;

a, c, d, f, g, i, j, j', k, l, n, o, p, q and t may be the same or different and are independently 0 or a positive integer, preferably, in most aspects;

b, e, r, r', s, h, h' and m may be the same or different and are independently 0 or 1;

mPEG is $H_3CO(-CH_2CH_2O)_u-$ and u is a positive integer, preferably from about 10 to about 2,300, and more preferably from about 200 to about 1000.

Within the above, it is preferred that $Y_{1-11}$ and $Y_{13}$ are O; $R_{3-8}$, $R_{12-21}$ and $R_{24}$ are each independently either hydrogen or $C_{1-6}$ alkyls, with methyl and ethyl being the most preferred alkyls and $R_9$ is preferably $CH_3$.

In a further aspect of the invention, the polymer portion of the conjugate can be one which affords multiple points of attachment for the L-asparaginase. A non-limiting list of such systems include:

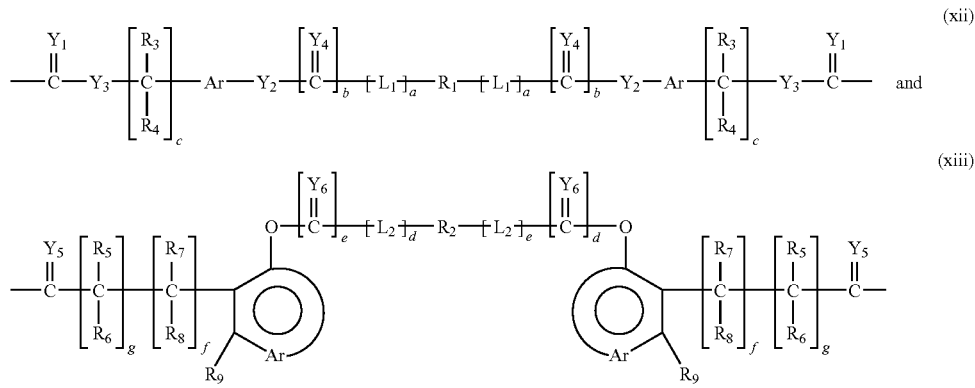

wherein all variables are the same as that set forth above.

The activated polymers which can be employed to make the L-asparaginase conjugates will naturally correspond directly with the polymer portions described above. The chief difference is the presence of a leaving or activating group, which facilitates the releasable attachment of the polymer system to an amine group found on the L-asparaginase. Thus, compounds (i)-(xiii) include a leaving or activating group such as: p-nitrophenoxy, thiazolidinyl thione, N-hydroxysuccinimidyl

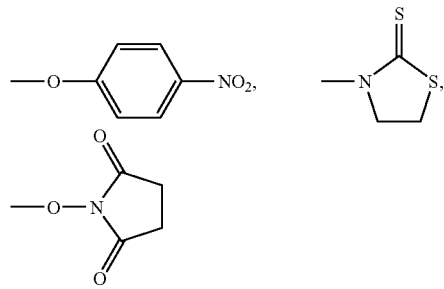

or other suitable leaving or activating groups such as, N-hydroxybenzotriazolyl, halogen, N-hydroxyphthalimidyl, imidazolyl, O-acyl ureas, pentafluorophenol or 2,4,6-tri-chlorophenol or other suitable leaving groups apparent to those of ordinary skill, found in the place where the L-asparaginase attaches after the conjugation reaction.

Some preferred activated PEGs include those disclosed in commonly assigned U.S. Pat. Nos. 5,122,614, 5,324,844, 5,612,460 and 5,808,096, the contents of which are incorporated herein by reference. As will be appreciated by those of ordinary skill such conjugation reactions typically are carried out in a suitable buffer using a several-fold molar excess of activated PEG. Some preferred conjugates made with linear PEGs like the above mentioned SC-PEG can contain, on average, from about 20 to about 80 PEG strands per enzyme. Consequently, for these, molar excesses of several hundred fold, e.g., 200-1000× can be employed. The molar excess used for branched polymers and polymers attached to the enzyme will be lower and can be determined using the techniques described in the patents and patent applications describing the same that are mentioned hereinbelow.

For purposes of the present invention, leaving groups are to be understood as those groups which are capable of reacting with an amine group (nucleophile) found on an L-asparaginase, e.g. on a Lys.

For purposes of the present invention, the foregoing is also referred to as activated polymer linkers. The polymer residues are preferably polyalkylene oxide-based and more preferably polyethylene glycol (PEG) based wherein the PEG is either linear or branched.

Referring now to the activated polymers described above, it can be seen that the Ar is a moiety which forms a multi-substituted aromatic hydrocarbon or a multi-substituted heteroaromatic group. A key feature is that the Ar moiety is aromatic in nature. Generally, to be aromatic, the π (pi) electrons must be shared within a "cloud" both above and below the plane of a cyclic molecule. Furthermore, the number of n electrons must satisfy the Huckle rule (4n+2). Those of ordinary skill will realize that a myriad of moities will satisfy the aromatic requirement of the moiety and thus are suitable for use herein with halogen(s) and/or side chains as those terms are commonly understood in the art.

In some preferred aspects of the invention, the activated polymer linkers are prepared in accordance with commonly-assigned U.S. Pat. Nos. 6,180,095, 6,720,3106, 5,965,119, 6624,142 and 6,303,569, the contents of which are incorporated herein by reference. Within this context, the following activated polymers are preferred:

11 12
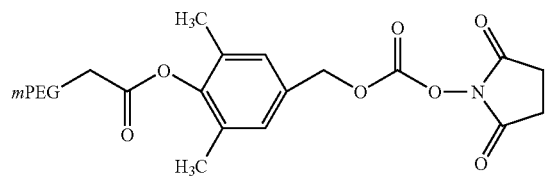 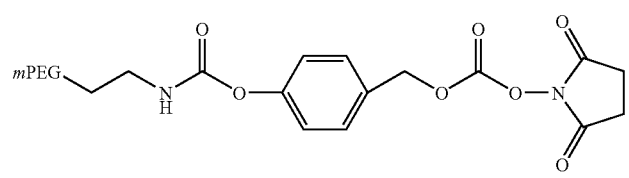
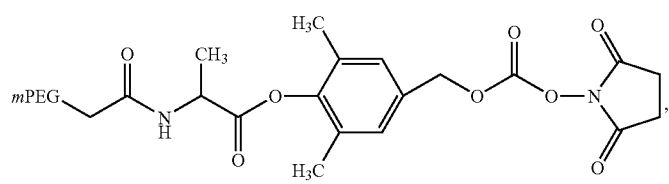
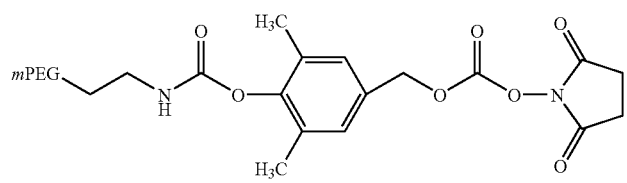
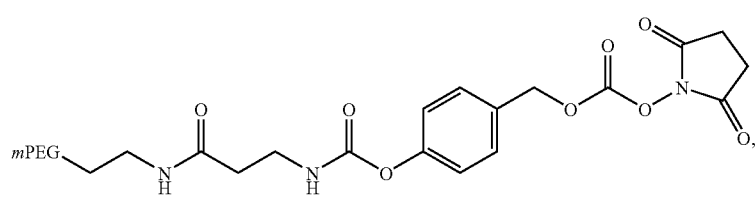
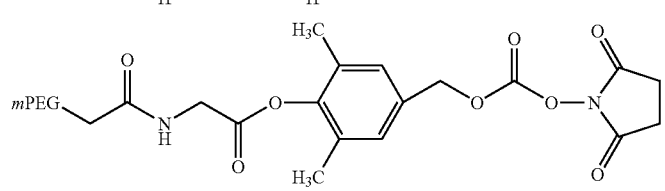
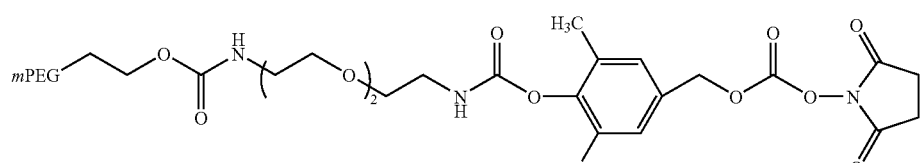
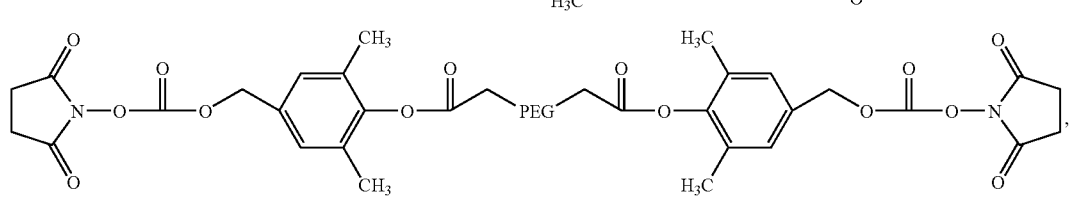
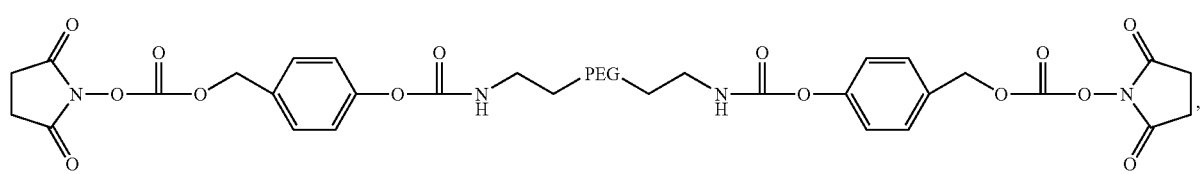
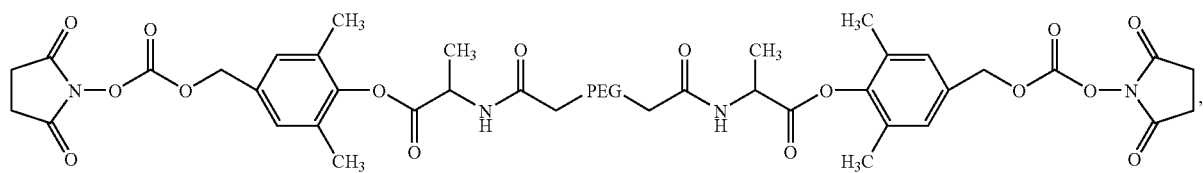

-continued

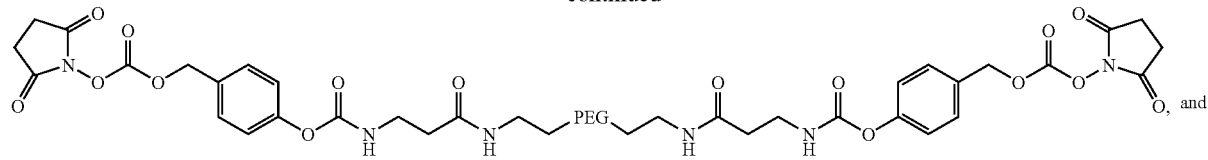

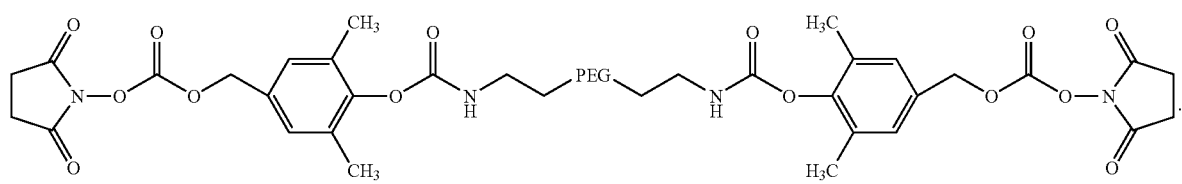

In one alternative aspect of the invention, L-asparaginase polymer conjugates are made using certain branched or bicine polymer residues such as those described in commonly assigned U.S. Pat. Nos. 7,122,189 and 7087,229 and U.S. patent application Ser. Nos. 10/557,522, 11/502,108, and 11/011,818. The disclosure of each such patent application is incorporated herein by reference. A few of the preferred activated polymers include:

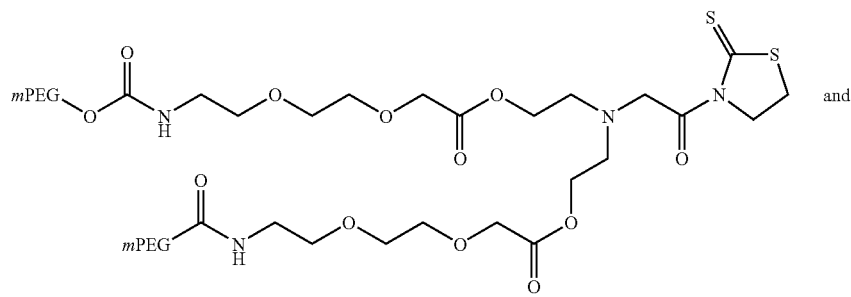

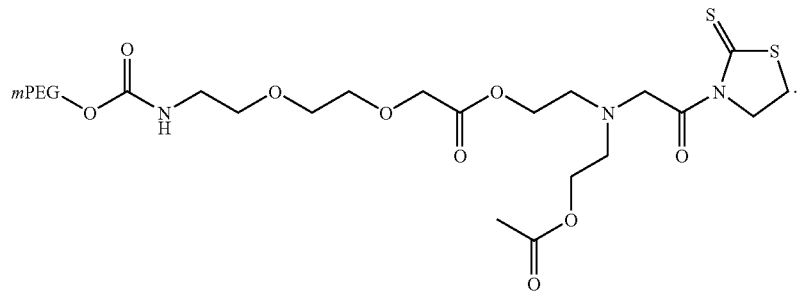

It should also be understood that the leaving group shown above is only one of the suitable groups and the others mentioned herein can also be used without undue experimentation.

In alternative aspects, the activated polymer linkers are prepared using branched polymer residues such as those described commonly assigned U.S. Pat. Nos. 5,643,575; 5,919,455 and 6,113,906 and 6,566,506, the disclosure of each being incorporated herein by reference. Such activated polymers correspond to polymer systems (v)-(ix) with the following being representative:

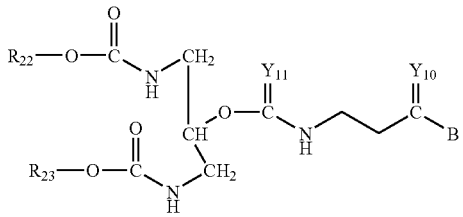

wherein B is L-asparaginase II and all other variables are as previously defined.

Substantially Non-Antigenic Polymers

As stated above, $R_{1-2}$, $R_{10-11}$, and $R_{22-23}$ are preferably each water soluble polymer residues which are preferably substantially non-antigenic such as polyalkylene oxides (PAO's) and more preferably polyethylene glycols such as mPEG. For purposes of illustration and not limitation, the polyethylene glycol (PEG) residue portion of $R_{1-2}$, $R_{10-11}$, and $R_{22-23}$ can be selected from among:

J-O—(CH$_2$CH$_2$O)$_u$—

J-O—(CH$_2$CH$_2$O)$_u$—CH$_2$C(O)—O—,

J-O—(CH$_2$CH$_2$O)$_u$—CH$_2$CH$_2$NR$_{25}$—, and

J-O—(CH$_2$CH$_2$O)$_u$—CH$_2$CH$_2$SH—, wherein:
u is the degree of polymerization, i.e. from about 10 to about 2,300;

$R_{25}$ is selected from among hydrogen, $C_{1-6}$ alkyls, $C_{2-6}$ alkenyls, $C_{2-6}$ alkynyls 3-$C_{3-12}$ branched alkyls, $C_{3-8}$ cycloalkyls, $C_{1-6}$ substituted aryls, $C_{2-6}$ substituted alkenyls, $C_{2-6}$ substituted alkynyls, $C_{3-8}$ substituted cycloalkyls, aryls substituted aryls, aralkyls, $C_{1-6}$ heteroalkyls, substituted $C_{1-6}$ heteroalkyls, $C_{1-6}$ alkoxy, phenoxy and $C_1$-6 heteroalkoxy, and J is a capping group, i.e. a group which is found on the terminal of the polymer and, in some aspects, can be selected from any of NH$_2$, OH, SH, CO$_2$H, $C_{1-6}$ alkyls, preferably methyl, or other PEG terminal activating groups, as such groups are understood by those of ordinary skill.

In one particularly preferred embodiment, $R_{1-2}$, $R_{10-11}$, and $R_{22-23}$ are selected from among,

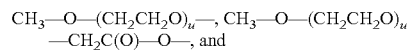
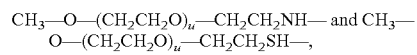

where u is a positive integer, preferably selected so that the weight average molecular weight from about 200 to about 80,000 Da. More preferably, $R_{1-2}$, $R_{10-11}$, and $R_{22-23}$ independently have an average molecular weight of from about 2,000 Da to about 42,000 Da, with an average molecular weight of from about 5,000 Da to about 40,000 Da being most preferred. Other molecular weights are also contemplated so as to accommodate the needs of the artisan.

PEG is generally represented by the structure:

and $R_{1-2}$, $R_{10-11}$, and $R_{22-23}$ preferably comprise residues of this formula. The degree of polymerization for the polymer represents the number of repeating units in the polymer chain and is dependent on the molecular weight of the polymer.

Also useful are polypropylene glycols, branched PEG derivatives such as those described in commonly-assigned U.S. Pat. No. 5,643,575 (the '575 patent), "star-PEG's" and multi-armed PEG's such as those described in Shearwater Corporation's 2001 catalog "Polyethylene Glycol and Derivatives for Biomedical Application". The disclosure of each of the foregoing is incorporated herein by reference. The branching afforded by the '575 patent allows secondary or tertiary branching as a way of increasing polymer loading on a biologically active molecule from a single point of attachment. It will be understood that the water-soluble polymer can be functionalized for attachment to the bifunctional linkage groups if required without undue experimentation.

For example, the conjugates of the present invention can be made by methods which include converting the multi-arm PEG-OH or "star-PEG" products such as those described in NOF Corp. Drug Delivery System catalog, Ver. 8, Apr. 2006, the disclosure of which is incorporated herein by reference, into a suitably activated polymer, using the activation techniques described in the aforementioned '614 or '096 patents. Specifically, the PEG can be of the formula:

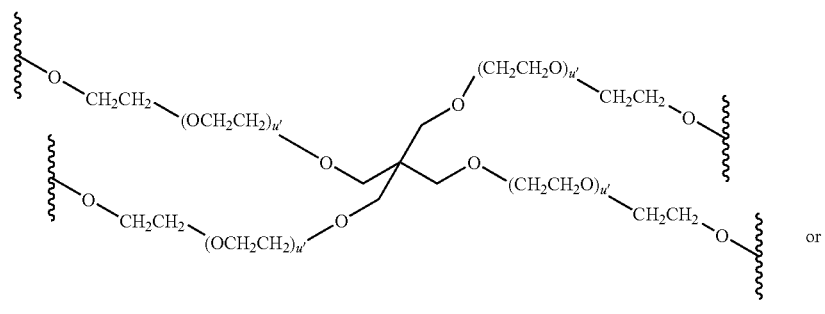

Star

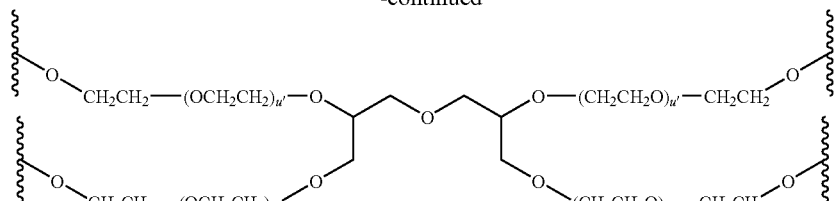

Multi-arm wherein:

u' is an integer from about 4 to about 455, to preferably provide polymers having a total molecular weight of from about 5,000 to about 40,000; and up to 3 terminal portions of the residue is/are capped with a methyl or other lower alkyl.

In some preferred embodiments, all 4 of the PEG arms are converted to suitable leaving groups, i.e. N-hydroxysuccinimidyl carbonate (SC), etc., for facilitating attachment to the recombinant protein. Such compounds prior to conversion include:

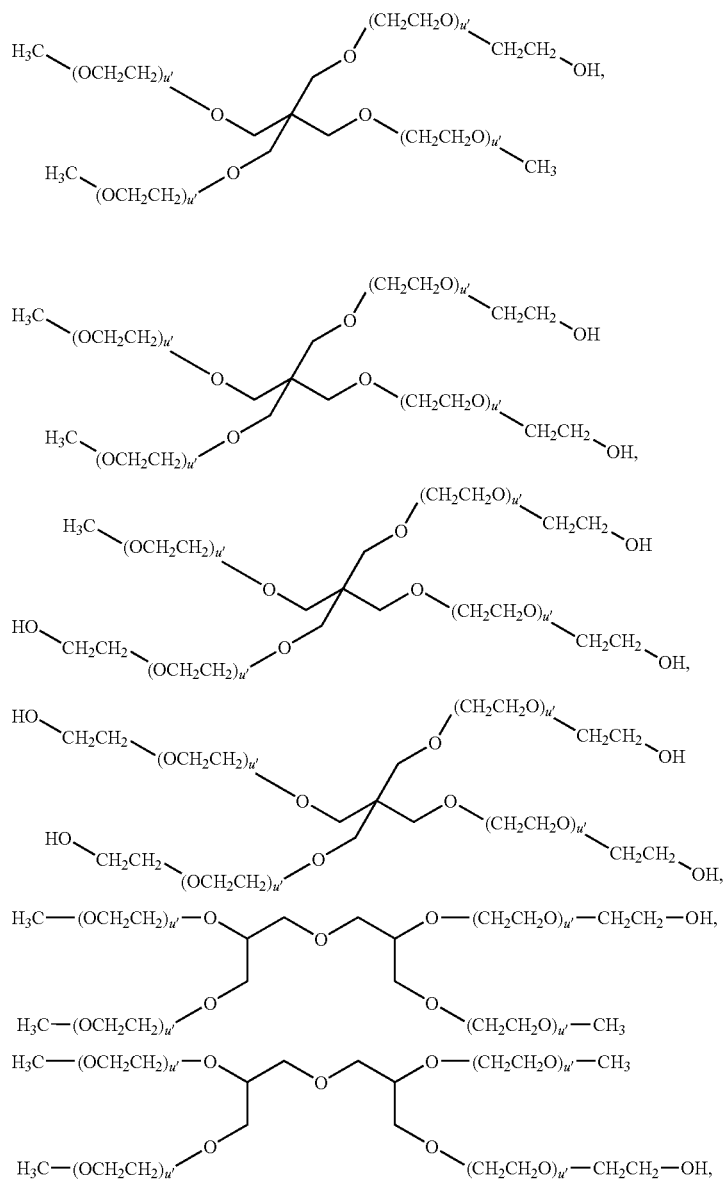

-continued

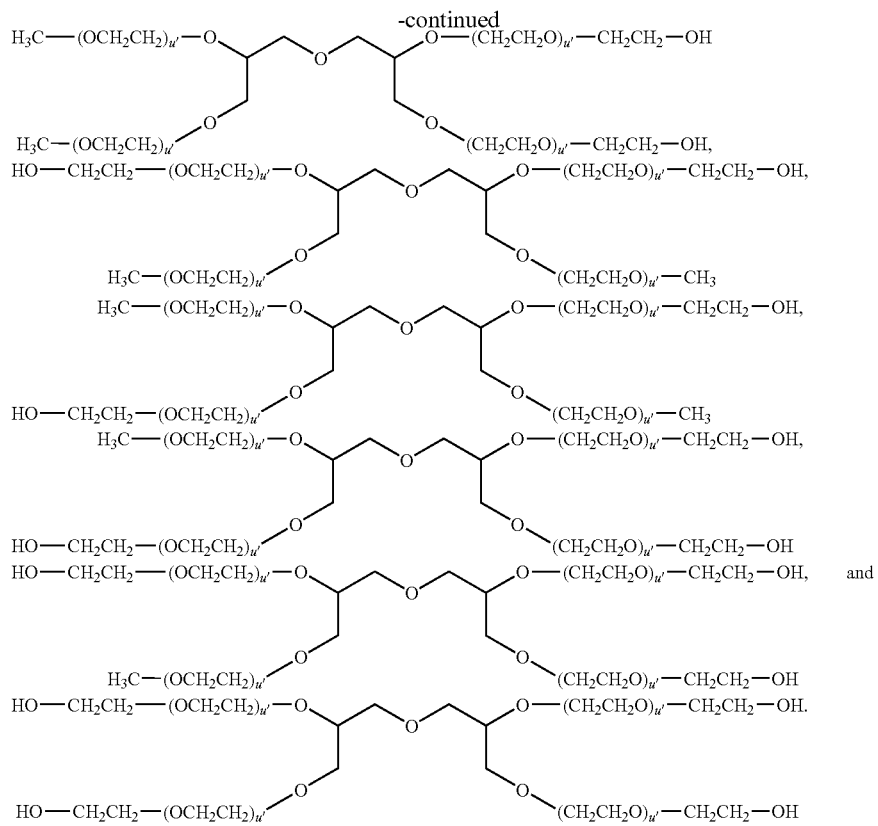

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

In a further embodiment, and as an alternative to PAO-based polymers, $R_{1-2}$, $R_{10-11}$, and $R_{22-23}$ are each optionally selected from among one or more effectively non-antigenic materials such as dextran, polyvinyl alcohols, carbohydrate-based polymers, hydroxypropylmeth-acrylamide (HPMA), polyalkylene oxides, and/or copolymers thereof. See also commonly-assigned U.S. Pat. No. 6,153,655, the contents of which are incorporated herein by reference. It will be understood by those of ordinary skill that the same type of activation is employed as described herein as for PAO's such as PEG. Those of ordinary skill in the art will further realize that the foregoing list is merely illustrative and that all polymeric materials having the qualities described herein are contemplated and that other polyalkylene oxide derivatives such as the polypropylene glycols, etc. are also contemplated.

Bifunctional Linker Groups:

In many aspects of the invention, $L_{1-6}$ and $L_8$ are linking groups which facilitate attachment of the polymer strands, e.g. $R_{1-2}$, $R_{10-11}$, and/or $R_{22-23}$. The linkage provided can be either direct or through further coupling groups known to those of ordinary skill. In this aspect of the invention, $L_{1-6}$ and $L_8$ may be the sane or different and can be selected from a wide variety of groups well known to those of ordinary skill such as bifunctional and heterobifunctional aliphatic and aromatic-aliphatic groups, amino acids, etc. Thus, $L_{1-6}$ and $L_8$ can be the same or different and include groups such as:

—[C(=O)]$_v$(CR$_{32}$R$_{33}$)$_t$—,

—[C(=O)]$_v$O(CR$_{32}$R$_{33}$)$_t$O—,

—[C(=O)]$_v$O(CR$_{32}$R$_{33}$)$_t$NR$_{36}$—,

—[C(=O)]$_v$O(CR$_{32}$R$_{33}$O)$_t$NR$_{36}$—,

—[C(=O)]$_v$NR$_{31}$(CR$_{32}$R$_{33}$)$_t$—,

—[C(=O)]$_v$NR$_{31}$(CR$_{32}$R$_{33}$)$_t$O—,

—[C(=O)]$_v$NR$_{31}$(CR$_{32}$R$_{33}$O)$_t$—,

—[C(=O)]$_v$NR$_{31}$(CR$_{32}$R$_{33}$O)$_t$(CR$_{34}$R$_{35}$)$_y$—,

—[C(=O)]$_v$NR$_{31}$(CR$_{32}$R$_{33}$O)$_t$(CR$_{34}$R$_{35}$)$_y$O—,

—[C(=O)]$_v$NR$_{31}$(CR$_{32}$R$_{33}$)$_t$(CR$_{34}$CR$_{35}$O)$_y$—,

—[C(=O)]$_v$NR$_{31}$(CR$_{32}$R$_{33}$)$_t$(CR$_{34}$CR$_{35}$O)$_y$NR$_{36}$—,

—[C(=O)]$_v$NR$_{31}$(CR$_{32}$R$_{33}$)$_t$NR$_{36}$—,

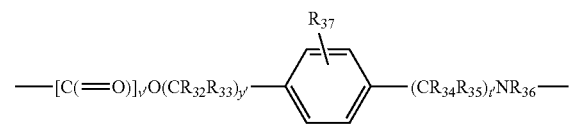

-continued

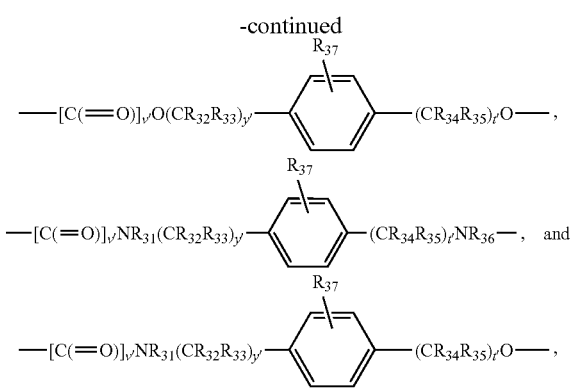

wherein:

$R_{31}$-$R_{37}$ are independently selected from the group consisting of hydrogen, amino, substituted amino, azido, carboxy, cyano, halo, hydroxyl, nitro, silyl ether, sulfonyl, mercapto, $C_{1-6}$ alkylmercapto, arylmercapto, substituted arylmercapto, substituted $C_{1-6}$ alkylthio, $C_{1-6}$ alkyls, $C_{2-6}$ alkenyl, $C_{2-6}$ alkynyl, $C_{3-19}$ branched alkyl, $C_{3-8}$ cycloalkyl, $C_{1-6}$ substituted alkyl, $C_{2-6}$ substituted alkenyl, $C_{2-6}$ substituted alkynyl, $C_{3-8}$ substituted cycloalkyl, aryl, substituted aryl, heteroaryl, substituted heteroaryl, $C_{1-6}$ heteroalkyl, substituted $C_{1-6}$heteroalkyl, $C_{1-6}$ alkoxy, aryloxy, $C_{1-6}$heteroalkoxy, heteroaryloxy, $C_{2-6}$ alkanoyl, arylcarbonyl, $C_{2-6}$ alkoxycarbonyl, aryloxycarbonyl $C_{2-6}$ alkanoyloxy, arylcarbonyloxy $C_{2-6}$ substituted alkanoyl, substituted arylcarbonyl, $C_{2-6}$ substituted alkanoyloxy, substituted aryloxycarbonyl, $C_{2-6}$ substituted alkanoyloxy, substituted and arylcarbonyloxy, wherein the sub substituents are selected from the group consisting of acyl, amino, amido, amidine, araalkyl, aryl, azido, alkylmercapto, arylmercapto, carbonyl, carboxylate, cyano, ester; ether, formyl, halogen, heteroaryl, heterocycloalkyl, hydroxy, imino, nitro, thiocarbonyl, thioester, thioacetate, thioformate, alkoxy, phosphoryl, phosphonate, phosphinate, silyl, sulfhydryl, sulfate, sulfonate, sulfamoyl, sulfonamide, and sulfonyl;

(t') and (y') are independently selected from zero or positive integers, preferably 1 to 6; and (v') is 0 or 1.

Preferably, $L_{1-6}$ and $L_8$, are selected from among:

—C(O)CH$_2$OCH$_2$C(O)—;

—C(O)CH$_2$NHCH$_2$C(O)—;

—C(O)CH$_2$SCH$_2$C(O)—;

—C(O)CH$_2$CH$_2$CH$_2$C(O)—, and

—C(O)CH$_2$CH$_2$C(O)—.

Alternatively, suitable amino acid residues can be selected from any of the known naturally-occurring L-amino acids is, e.g., alanine, valine, leucine, etc. and/or a combination thereof, to name but a few. $L_{1-6}$ and $L_8$ can also include a peptide which ranges in size, for instance, from about 2 to about 10 amino acid residues.

Derivatives and analogs of the naturally occurring amino acids, as well as various art-known non-naturally occurring amino acids (D or L), hydrophobic or non-hydrophobic, are also contemplated to be within the scope of the invention.

A Moieties

1. Leaving or Activating Groups

In those aspects where A is an activating group, suitable moieties include, without limitation, groups such as N-hydroxybenzotriazolyl, halogen, N-hydroxyphthalimidyl, p-nitrophenoxyl, imidazolyl, N-hydroxysuccinimidyl; thiazolidinyl thione, O-acyl ureas, pentafluorophenoxyl, 2,4,6-trichlorophenoxyl or other suitable leaving groups that will be apparent to those of ordinary skill.

For purposes of the present invention, leaving groups are to be understood as those groups which are capable of reacting with a nucleophile found on the desired target, i.e. a biologically active moiety, a diagnostic agent, a targeting moiety, a bifunctional spacer, intermediate, etc. The targets thus contain a group for displacement, such as NH$_2$ groups found on proteins, peptides, enzymes, naturally or chemically synthesized therapeutic molecules such as doxorubicin, spacers such as mono-protected diamines. It is to be understood that those moieties selected for A can also react with other moieties besides biologically active nucleophiles.

2. Functional Groups

A can also be a functional group. Non-limiting examples of such functional groups include maleimidyl, vinyl, residues of sulfone, hydroxy, amino, carboxy, mercapto, hydrazide, carbazate and the like which can be attached to the bicine portion through an amine-containing spacer. Once attached to the bicine portion, die functional group, (e.g. maleimide), can be used to attach the bicine-polymer to a target such as the cysteine residue of a polypeptide, amino acid or peptide spacer, etc.

3. Alkyl Groups

In those aspects of formula (I) where A is an alkyl group, a non-limiting list of suitable groups consists of $C_{1-6}$ alkyls, $C_{2-6}$ alkenyls, $C_{2-6}$ alkynyls, $C_{3-19}$ branched alkyls, $C_{3-8}$ cycloalkyls, $C_{1-6}$ substituted alkyls, $C_{2-6}$ substituted alkenyls, $C_{1-6}$ substituted alkynyls, $C_{3-8}$ substituted cycloalkyls, aralkyls, $C_{1-6}$ heteroalkyls, and substituted $C_{1-6}$heteroalkyls.

Z Moieties and their Function

In one aspect of the invention 7 is $L_7$-C($=$Y$_{12}$) wherein $L_7$ is a bifunctional linker selected from among the group which defines $L_{1=6}$, and Y$_{12}$ is selected from among the same groups as that which defines Y$_1$. In this aspect of the invention, the Z group serves as the linkage between the L-asparaginase and the remainder of the polymer delivery system. In other aspects of the invention, Z is a moiety that is actively transported into a target cell, a hydrophobic moiety, and combinations thereof. The Z when present can serve as a bifunctional linker, a moiety that is actively transported into a target cell, a hydrophobic moiety, and combinations thereof.

In this aspect of the invention, the releasable polymer systems are prepared so that in hydrolysis cleaves the polymer from the L-asparaginase and releases the enzyme into the extracellular fluid, while still linked to the Z moiety. For example, one potential Z-B combination is leucine-L-asparaginase Preparation of L-Asparaginase Conjugates For purposes of illustration, suitable conjugation reactions include reacting L-asparaginase with a suitably activated polymer systems described herein. The reaction is preferably carried out using conditions well known to those of ordinary skill for protein modification, including the use of a PBS buffered system, etc. with the pH in the range of about 6.5-8.5. It is contemplated that in most instances, an excess of the activated polymer will be reacted with the L-asparaginase.

Reactions of this sort will often result in the formation of conjugates containing one or more polymers attached to the L-asparaginase. As will be appreciated, it will often be desirable to isolate the various fractions and to provide a more homogenous product. In most aspects of the invention, the reaction mixture is collected, loaded onto a suitable column resin and the desired fractions are sequentially eluted off with increasing levels of buffer. Fractions are analyzed by suitable analytical tools to determine the purity of the conjugated protein before being processed further. Regardless of the synthesis route and activated polymer selected, the conjugates will conform to Formula (I) as defined herein. Some of the preferred compounds which result from the synthetic techniques described herein include:

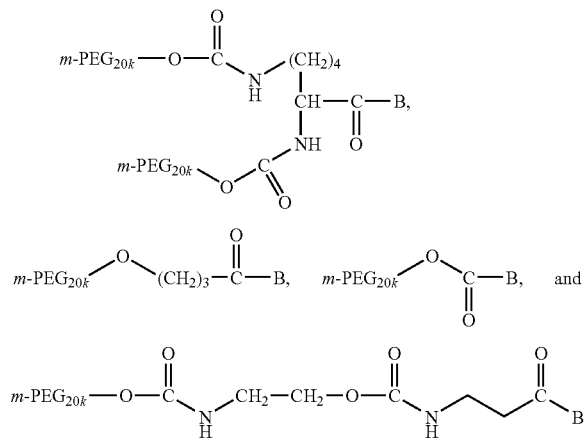

wherein B is L-asparaginase.

Still further conjugates made in accordance with the present invention include:

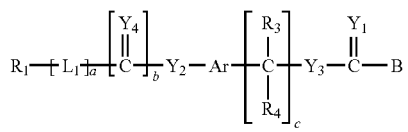

wherein all variables are the same as that set forth above. For example, some of embodiments included in the conjugates are selected from the group consisting of:

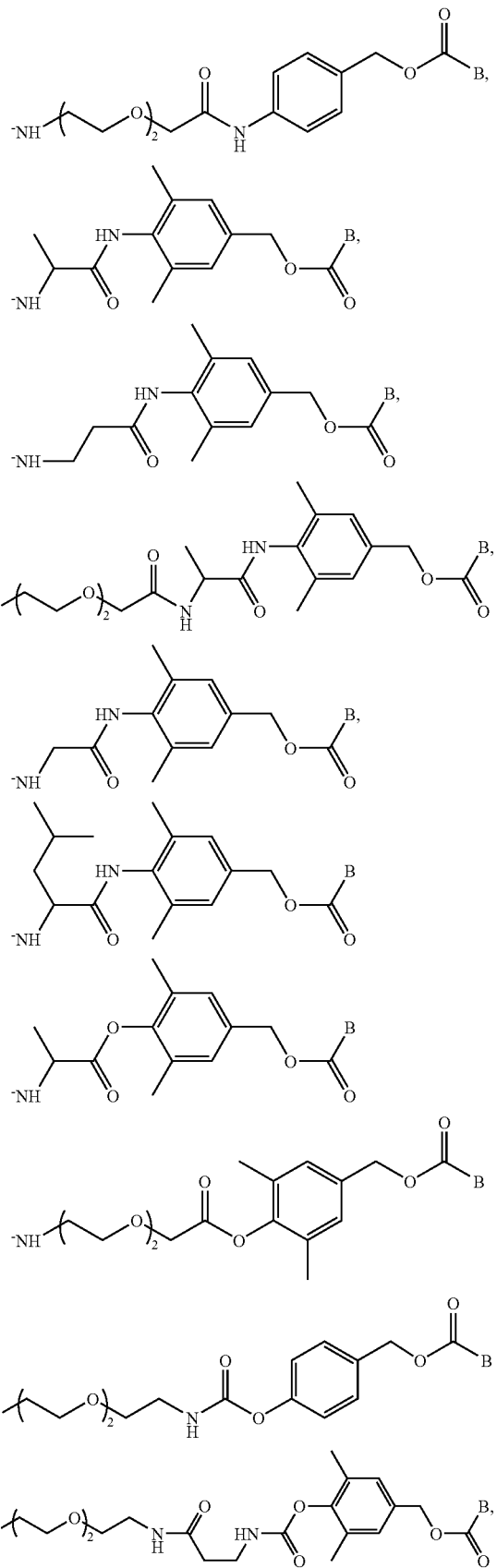

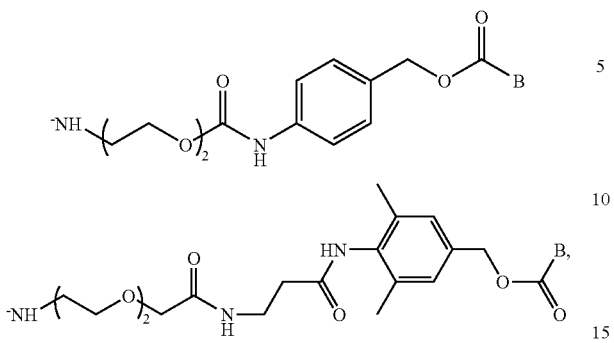
wherein B is L-asparaginase.
Further conjugates include:
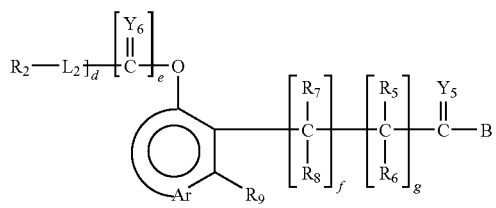
wherein B is L-asparaginase. A non-limiting list employed in the conjugates are among
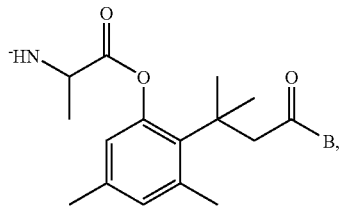
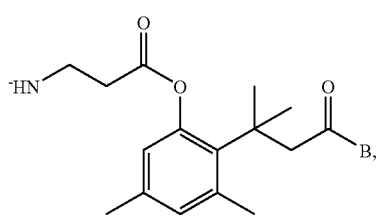
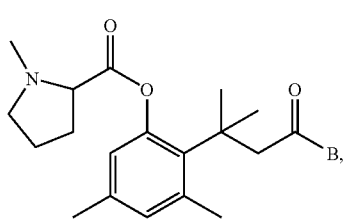
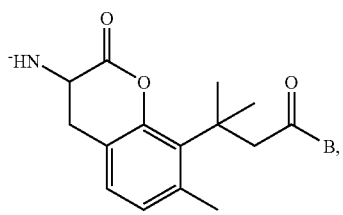
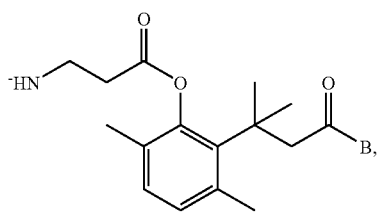
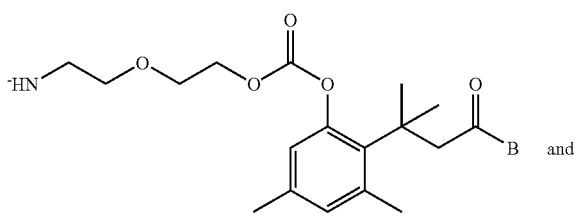
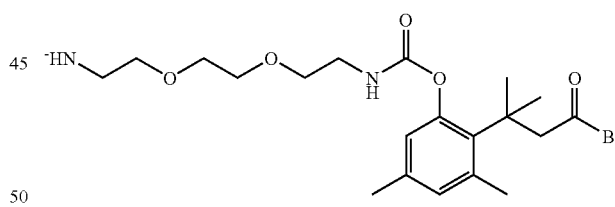 and
wherein B is L-asparaginase.
A particularly preferred conjugate is:
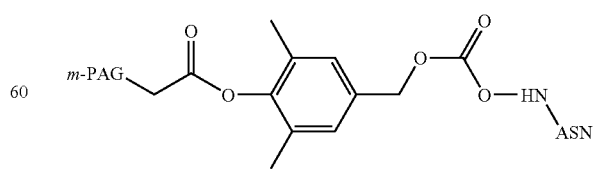
wherein the molecular weight of the mPEG is from about 10,000 to about 40,000.

When the bicine-based polymer systems are used, two preferred conjugates are:

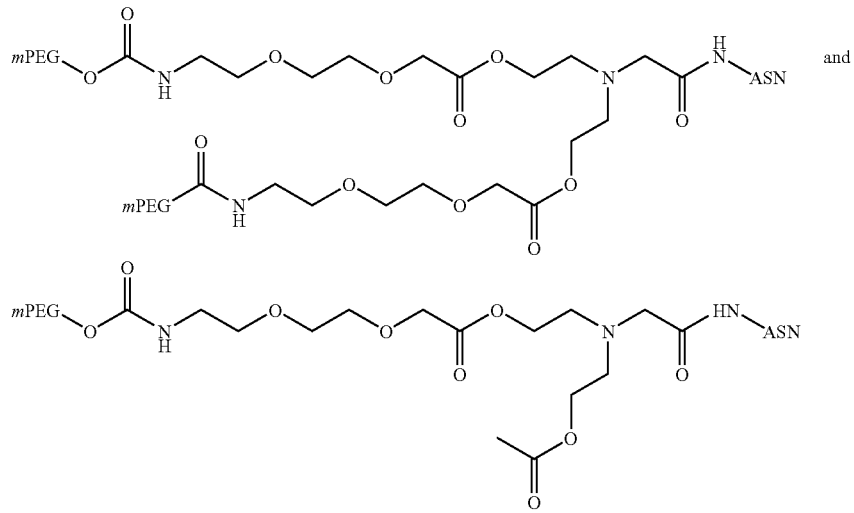

wherein the molecular weights of the mPEG are the same as above.

It is noted that PEGylation of L-asparaginase will be empirically optimized for total PEG attachments per protein, PEG polymer size, and PEG linker design. Key characteristics of the PEGylated L-asparaginase for evaluation of PEGylation optimization include both in vitro assays (e.g., enzyme activity and stability) and in vivo assays (e.g., pharmacokinetics and pharmacodynamics).

Methods of Treatment

The L-asparaginase produced by the DNA, vectors and host cells described herein is useful for all of the methods and indications already art-known for Elspar® (Merck & Co., Inc) and Oncaspar® (Enzon Pharmaceuticals, Inc.). Thus, the inventive L-asparaginase II enzyme, whether polyalkylene oxide conjugated, or as an unconjugated protein is administered to a patient in need thereof in an amount that is effective to treat a disease or disorder or other condition that is responsive to such treatment. The artisan will appreciate suitable amounts, routes of administration and dosing schedules extrapolated from the known properties of Elspar® and Oncaspa®.

EXAMPLES

The following non-limiting examples set forth hereinbelow illustrate certain aspects of the invention.

Example 1

Sequencing of L-Asparagine Amidohydrolase, Type EC-2, EC 3.5.1.1: *E. coli* L-Asparaginase II Protein In order to obtain the amino acid sequences of the L-asparaginase II enzymes commercially available from Merck & Co. and Kyowa Hakko Kogyo Co., respectively, these proteins were subject to protein sequence analysis and compared to the sequence of the published *E. coli* K-12 ansB gene (GenBank Accession Number M34277).

L-asparaginase II was sequenced as follows. An aliquot of 2 mL of L-asparaginase II (80 mg/mL; Merck) was diluted in reagent grade water to yield a diluted solution with a protein concentration of 5.0 mg/mL. The diluted solution was filtered through a 0.22 μm filter into vials in order to reduce bioburden before conducting the protein sequence analysis. Similarly 100 mg of L-asparaginase II (Kyowa Hakko Kogyo) was dissolved in 20 mL of reagent grade water to yield a diluted solution of 5.6 mg/mL and sterile filtered. Quantitative amino acid analyses, N-terminal sequence determinations, peptide mapping, and mass spectrometry were used to determine the complete sequences of the two proteins. Tryptic digest, chymotryptic digest, Lys-C digest and cyanogen bromide (CnBr) fragments were prepared and separated by high pressure liquid chromatography ("HPLC"), and mass spectrometry and amino acid sequencing were performed on the isolated peptides. The completed analyses demonstrated an apparent sequence identity between the two commercial L-asparaginase II enzymes. However, four amino acid positions differed from the gene sequence derived asparaginase from E. coli K-12. These four differing positions are shown by Table 1, below.

TABLE 1

| Residue Position | 27 | 64 | 252 | 263 |
|---|---|---|---|---|
| Merck and KH | Ala | Asp | Thr | Asn |
| K12 AnsB | Val | Asn | Ser | Thr |

Example 2

Construction of *E. coli*_Strain EN538 Expressing Recombinant L-Asparaginase II

The gene encoding *E. coli* K-12 ansB L-asparaginase II was adapted to express L-asparaginase II with the residue substitutions illustrated by Table 1 of Example 1, as follows. The 326 mature amino acid sequence L-asparaginase II of *E. coli* K-12 ansB is encoded in a 978 base pair segment as reported by Jennings M P and Beacham I R (1990 *J Bacteriol* 172: 1491-1498; GeneBank No. M34277). The ansB gene, which includes a 22 amino acid signal peptide preceding then mature protein, was cloned from another *E. coli* K-12 strain (GX1210; obtained from Genex Corporation) by conventional polymerase chain reaction (PCR) methods. Specifically, the oligonucleotides 5'-TACTGAATTCATG-GATTTTTCAAAAAGACGGCA-3' (SEQ ID NO: 4) and 5'-ACAGTAAGCTTAGTACTGATTGAAGATCTGCTG-3' (SEQ ID NO: 5) were employed as primers using a Perkin Elmer Gene Amp 9600 thermocycler, Taq polymerase, and standard reagents with these cycling parameters: 30 sec 94° C., 30 sec 40° C., 1 min 72° C., for 25 cycles.

The amplified ~1 kb band was purified on TBE agarose gel electrophoresis, digested with Eco RI and Hind III, and cloned into the bacteriophage vector M13 mp8. The DNA sequence of the ansB gene [Genebank No. M34277] was confirmed by manual DNA dideoxy sequencing methods. The cloned ansB gene was used next in site-directed mutagenesis to change four codons of ansB gene [GTG to GCG at base 530; AAT to GAT at base 640; TCT to ACT at base 1205 and ACC to AAC at base 1239] to encode the alternate amino acids (Val27Ala; Asn64Asp; Ser252Thr; and Thr263Asn) using the Amershan RPN 1523 version 2 mutagenesis kit as described by Whitlow, and Filpula [Single Chain Fvs, In Tumour Immunology. A Practical Approach, Ed. G. Gallagher, R. C. Rees, and C. W. Reynolds, 1993, Oxford University Press, pp 279-291].

Specifically, mutagenic oligonucleotides employed were 5'-CAACTTTACCCGCTGTGTAGTTAG4-3' (SEQ ID NO: 6) for Val27Ala change; 5'-CAGCCAGACATCATCGT-TCATGTC-3' (SEQ ID NO: 7) for Asn64Asp change; 5'-GTCGAACACAGTTTTATACAGGTTGC-3' (SEQ ID NO: 8) for Ser252Thr change; 5'-CTGCAGTAC-CGTTTTTCGCGGCGG-3' (SEQ ID NO: 9) for Thr263Asn change. All four changes were made in a single batch and DNA sequencing confirmed the modified ansB gene sequence [designated herein as the ansB* gene (SEQ ID NO: 2)].

Cloning of the ansB* gene into plasmid pET-27b+ (Novagen Corporation) was accomplished by introducing the flanking restriction sites, NdeI and BamHI, at the 5' and 3' termini of the gene, respectively, by PCR amplification. Following digestion of the synthetic DNA with the restriction enzymes NdeI and BamHI, the 1 kilobase gene was ligated via T4 DNA ligase into the plasmid vector pET-276b(+) plasmid which had also been digested with these two enzymes. The recombinant plasmid was introduced into *E. coli* strain BLR (DE3) by electroporation using a BTX Electro Cell Manipulator 600 according to the manufacturer's instructions.

The pET vector construction places the ansB* tone behind a T7 promoter which is inducible as a consequence of IPTG addition. IPTG induces expression of the chromosomal T7 RNA polymerase gene under the control of a lacUV5 promoter and the T7 RNA polymerase then transcribes the ansB* gene yielding high level expression of the ansB* protein product.

The transformation mixture was plated on LB agar plates containing kanamycin (15 g/ml) to allow for selection of colonies containing the plasmid pET-27b(+)/ansB*. This is designated as plasmid pEN537, as illustrated by FIG. 1. Isolated colonies were further purified by plating and analyzed for IPTG inducible gene expression by standard methods such as those described in Novagen pET System Manual Ninth Edition. The gene sequences were verified using an Applied Biosystems Prism310 Genetic Analyzer.

Example 3

Expression of Recombinant L-Asparaginase II and Partial Characterization of the Enzyme Strain EN538 was cultured in LB medium at 37° C. with kanamycin (15 µg/ml). At $OD_{600}$ of about 0.8, IPTG (1 mM) was added to the culture and induction of gene expression was allowed to progress for either 2, 3, or 4 hr. SDS-PAGE analysis of the culture confirmed high level expression of the 34.6 kDa ansB* polypeptide. Western blotting using anti-*E. coli* asparaginase II rabbit polyclonal antibody confirmed that the major induced protein band on SDS-PAGE was L-asparagase II.

Since L-asparaginase II is normally secreted into the periplasmic space following signal peptide removal, additional experiments were conducted to examine location of the asparaginase in the cells or medium. The culture was centrifuged and the pelleted cells were resuspended in a lysozyme solution to disrupt the cell walls before examining the soluble and insoluble cell associated proteins, plus the proteins released into the growth medium during culture, by SDS-PAGE.

These analyses demonstrated that either a 3 or 4 hr induction at 37° C. provides near maximal ansB* expression of about 30% of total cell proteins. At least 70% of the asparaginase can be solubilized from the cell pellet by lysozyme treatment. The amount of asparaginase released into the growth medium during culture is about 25% of the total asparaginase expressed.

The solubilized asparaginase released from the periplasm by lysozyme treatment was further examined for enzyme activity using an RP-HPLC assay that measures aspartic acid the product of the asparaginase reaction from the substrate, asparagine. Enzyme activity in crude extracts from the IPTG induced samples was about 60 IU/mg, while only about 2 IU/mg in samples prepared from uninduced cultures. Since the protein is only about 20% pure at this stage, this compares well to the reported specific activity of pure asparaginase II (~250-300 IU/mg). N-terminal sequence analysis of this asparaginase preparation was also achieved using an Applied BioSystems PROCISE protein sequencer. The N-terminal sequence LPNITILATGGTIAGGGDSA (SEQ ID NO: 10) matches exactly the predicted N-terminal protein sequence of mature, correctly processed, asparaginase. LC-MS analysis (Jupiter C-18 revered-phase column) was also performed on this sample. The principal protein species demonstrated a mass of 34,592 which exactly matches the predicted mass as mature ansB* asparaginase. No evidence of a protein species bearing norleucine substitutions was observed.

Example 4

Protein Coding Sequences of L-Asparaginase II (ANSB & ANSB* Genes) from pEN537 Plasmid and *E. coli* BLR Chromosome Chromosomal DNA was prepared from *E. coli* BLR (DE3) [obtained from Novagen Corporation; Cat. No. 69208-3]. A 2 ml culture of BLR grown in LB medium with kanamycin (15 µg/ml) at 37° C. was centrifuged for 2 min a microfuge and cell pellet was resuspended in 0.5 ml of STET buffer. Phenol/chloroform (0.5 ml) was added and the mixture was vortexed and centrifuged for 5 min at room temperature. The supernatant was collected and mixed with 50 μL of 3 M sodium acetate and 1 ml of ethanol. After incubating on ice for 10 min, the DNA was pelleted by centrifugation and resuspended in 100 μl of water. PCR was conducted on the sample to isolate the chromosomal ansB gene. The PCR reaction mixture contained 5 μl of 10× of High Fidelity PCR buffer, 5 μl of 10 mM-1 dNTP mixture 1 μl of 50 mM $MgSO_4$, 0.5 μl (50 μpmol) of oligonucleotide 5'-GATCCATATG-GAGTTTTTCAAAAAGACGGCAC-3' (SEQ ID NO: 11), 0.5 μl (50 pmol) of oligonucleotide 5'-GTACGGATCCT-CATTAGTACTGATTGAAGATC-3' (SEQ ID NO: 12), 1 μl of BLR DNA, 36 μl of distilled water, and 1 μl of Platinum Taq High Fidelity polymerase. The PCR product was cloned using the commercial TOPO cloning system obtained from Invitrogen Corporation and conducted as described by the manufacturer.

The cloning reaction using the PCR product and the TOPO TA vector was conducted in 6 μl at room temperature for 30 min. The ligation product of the reaction was transformed in competent TOP10 *E. coli* cells and plated ion LB agar plates with kanamycin selection. DNA sequence analysis of the cloned ansB BLR chromosomal gene and the pENS537 ansB* gene was conducted on the plasmids using an Applied Biosystems Prism 310 Genetic Analyzer. Both strands were sequenced. The coding sequences of the BLR ansB gene and pEN537 ansB* gene differ by 29 mismatched base assignments in the mature protein coding sequences. However, none of these base substitutions resulted in an alteration in the amino acid sequence due to codon degeneracy. The encoded ansB protein from BLR and the encoded ansB* protein from pEN537 was confirmed to be identical in amino acid sequence. All 326 positions were shown to be identical in these two asparaginase proteins.

Example 5

Purification from Cells and Culture Medium

The following process was adapted from Harms et al., 1991 *Protein Expression and Purification* 2: 144-150.

Cultures of *E. coli* strain EN 538, as described above, are grown in Luria broth in the presence of kanamycin (15 μg/ml) at 37° C., in a shaker incubator. At an $OD_{660}$ of 0.8, IPTG is added to a final concentration of 1 mM, and growth continued for an additional 4 h. Cells are harvested by centrifugation. For analytical purposes, 2-ml cultures are used.

To make cell extracts, the pellets are suspended in 1 ml disruption buffer (50 mM KPO, pH 7.5, 1 mM EDTA, 0.5 mM dithiothreitol] and cells disrupted by microfluidization. Cell debris is removed by centrifugation and the supernatant fluid is assayed for L-asparaginase II activity and also used to assess enzyme production by polyacrylamide gel electrophoresis (SDS PAGE). Osmotic shock fractionation is carried out as described by Boyd et al., 1987, *Proc. Natl. Acad. Sci. USA* 84:8525-8529, incorporated by references herein. In brief the pellet is suspended in 2 ml spheroblast buffer (0.1 M Tris-HCl, pH 8.0, 0.5 M sucrose, 0.5 mM EDTA), incubated on ice for 5 min, and centrifuged. The pellet is warmed to room temperature, resuspended in 0.3 ml ice-cold water, incubated on ice for 5 min, and again centrifuged. The supernatant periplasmic fraction is used without further treatment for activity determination and electrophoresis.

Enzyme Purification

For large-scale L-asparaginase II preparations cells are grown in batch cultures (10 liters) and subjected to osmotic shock as above. Per liter of culture volume 50-100 ml spheroblast buffer and 30-40 ml water are employed. The following protocol starts with the periplasmic extract obtained from a 2-liter culture. All steps are performed at 5-10° C.

Ammonium Sulfate Fractionation

To 100 μml of supernatant fluid 29.5 g solid ammonium sulfate is added to give 50% saturation. After 2 hours the precipitate is removed by centrifugation, and the pellet discarded. The supernatant was brought to 90% saturation with ammonium sulfate (27.2 g to 100 ml). After the pellet stood overnight it is collected by centrifugation, dissolved in a few milliliters of 25 mM piperazine-HCl buffer, pH 5.5, and dialyzed against the same buffer. This same process is also applied to the remaining cell culture medium to recover secreted L-asparaginase II.

Chromatofocusing

A 1×30-cm column of Poly-buffer exchanger PBE 94 was equilibrated with 200 ml of the above piperazine-HCl buffer (starting buffer). After the sample solution (10 ml) is applied, the column is eluted with 200 ml elution buffer (Polybuffer 74, diluted 10-fold with $H_2O$ and adjusted to pH 4.0 with HCl) at a flow rate of 30 ml/h. Fractions of 2 ml are collected and assayed for L-asparaginase II activity after appropriate dilution of 20-μl samples. The asparaginase-containing fractions are pooled and dialyzed against saturated ammonium sulfate solution. The enzyme pellet is washed with 90% ammonium sulfate and stored as a suspension in this medium.

Example 6

Purification from Cells and Culture Medium

Cultures of *E. coli* strain EN538, as described above, are grown in culture medium [e.g., as described in Filpula, D., McGuire, J. and Whitlow, M. (1996) Production of single-chain Fv monomers and multimers, In Antibody Engineering: A Practical Approach (J. McCafferty, H. Hoogenboom, and D. J. Chiswell, eds.; Oxford University Press, Oxford, UK) pp. 253-268] in the presence of kanamycin (15 μg/ml) at 25° C. to 37° C., in a fermenter. At an $OD_{660}$ of 20 to 200 IPTG is added to a final concentration of 0.1-1 mM, and growth continued for an additional 1-12 h. Cells are harvested by centrifugation and passed through a Manton-Gaulin cell homogenizer. The cell lysate is centrifuged at 24,300 g for 30 min at 6° C. and the supernatant is collected and subjected to ultrafiltration/diafiltration, and the conductivity is adjusted to 3 mS. The pH of the lysate is adjusted to 4.1 with 25% acetic acid and diafiltered with buffer 5 mM sodium acetate, 25 mM 1NaCl, pH 4.1.

The asparaginase is captured on S-Sepharose cation exchange column chromatography. The bound asparaginase is eluted with 12.5 mM potassium phosphate, 25 mM NaCl, pH 6.4 (buffer NK64).

The collected asparaginase peak fractions from S-Sepharose chromatography are pooled and 0.1% Tween80 is added and incubated for 20 min at room temperature. One volume of buffer NK64 is added and the sample is loaded onto a Q-Sepharose column. The Q column is washed with Q-25 buffer (25 mM NaCl, 10 mM potassium phosphate pH 6.4) and the asparaginase is then eluted with buffer Q-135 (135 mM NaCl in 10 mM potassium phosphate pH 6.4).

To the pooled enzyme fractions is added magnesium sulfate powder to a final concentration of 0.25 M and is loaded onto a phenyl hydrophobic interaction column pre-equilibrated with 0.25 M $MgSO_4$ in 10 mM potassium phosphate, pH 7.8. The asparaginase is collected in the flow through fraction and diafiltered in a Filtron unit using a 30 kDa molecular weight cut-off polysulfone membrane with the buffer 75 mM NaCl, 1 mM potassium phosphate pH 7.2.

The asparaginase fraction is diluted with an equal volume of water and loaded onto a hydroxyapatite column. Impurities are removed with elution with buffer H15 (50 mM NaCl, 15 mM potassium phosphate, pH 7.8). The purified asparaginase is eluted with buffer H150 (50 mM NaCl, 150 mM potassium phosphate, pH 7.8).

Example 7

Purification from Cells and Culture Medium

Cultures of *E. coli* strain EN538, grown, induced, and homogenized as described in Example 6, are diafiltered against 20 mM sodium acetate, 40 mM NaCl, pH 4.6 with 8 product volumes with a 50 kDa Microgon hollow fiber at a flow rate of 2.9 L/min, 16 psi until the $A_{280}$ is less than 0.1 and conductivity is 5 mS. The product is filtered using a 0.22 μm membrane.

Cation exchange chromatography is conducted with a Poros-4HS column. The column is equilibrated in 20 mM sodium acetate, ph 4.6, 40 mM NaCl. The diafiltered clarified media is loaded at 0.5 column volume (CV)/min and the column is washed with 5 CV of 20 mM sodium acetate, pH 4.6, 40 mM NaCl. The asparaginase is eluted with 20 mM sodium acetate, pH 4.6, 135 mM NaCl.

To the above product is added 0.2 M dibasic sodium phosphate, pH 9.2 to adjust the pH to 6.3. The sample is then diafiltered against 10 mM sodium phosphate, pH 6.3 with a 50 kDa Microgon hollow fiber filter at a flow rate of 0.74 L/min 16.5 psi.

Anion exchange chromatography is conducted on TMAE Fractogel. The column is equilibrated in 10 mM sodium acetate, pH 6.4. The diafiltered cation column eluate is loaded at 0.5 CV/min and the column is washed with 5 CV of 10 mM sodium acetate, pH 6.4. The column is further washed with 5 CV of 10 mM sodium acetate, pH 6.4, 25 mM NaCl. The asparaginase is eluted with 10 mM sodium acetate pH 6.4, 100 mM NaCl.

The product is diafiltered against 10 mM sodium phosphate, pH 7.5 with a 50 kDa membrane to a concentration of 40 mg/ml and filtered through a 0.22 μm membrane.

DEPOSIT STATEMENT

Cultures of the following biological materials have been deposited with the following international depository(ies):

American Type Culture Collection (ATCC)

10801 University Boulevard, Manassas, Va. 20110-2209, U.S.A.

under conditions that satisfy the requirements of the Budapest Treaty on the International Recognition of the Deposit of Microorganisms for the Purposes of Patent Procedure.

| International Depository Accession | | |
| --- | --- | --- |
| Organism/vector | ATCC Number | Date of Deposit |
| *E. coli*/EN538 | PTA 7490 | April 2006 |

We claim:

1. A recombinant *Escherichia coli* host cell for producing an *Escherichia coli* L-asparaginase II enzyme, comprising an *Escherichia coli* host cell chromosome and at least one copy of a recombinant extrachromosomal vector, wherein the recombinant extrachromosomal vector encodes a subunit of the L-asparaginase II enzyme, wherein the host cell chromosome also encodes the same subunit of the L-asparaginase II enzyme, and wherein the host cell chromosome does not encode any other isoform of L-asparaginase II, wherein the encoded L-asparaginase II subunit comprises SEQ ID NO: 1; and the recombinant extrachromosomal vector comprises a DNA molecule comprising SEQ ID NO: 2.

2. The recombinant *Escherichia coli* host cell of claim 1, wherein the extrachromosomal vector is a plasmid.

3. The recombinant *Escherichia coli* host cell of claim 1 wherein the DNA molecule is operatively connected to a suitable promoter.

4. The recombinant *Escherichia coli* host cell of claim 3 wherein the promoter is selected from the group consisting of T7, araB, $P_R/P_L$, phoA, trc, and trp promoters.

5. The recombinant *Escherichia coli* host cell of claim 3 wherein the recombinant extrachromosomal vector further comprises an operator, ribosome binding site, signal sequence, transcriptional terminator, antibiotic selection marker, origin of replication, and a regulated copy of the repressor.

6. The recombinant *Escherichia coli* host cell of claim 3 wherein the host cell chromosome comprises a DNA molecule according to SEQ ID NO:3.

7. An isolated nucleic acid molecule encoding an L-asparaginase II enzyme subunit of SEQ ID NO: 1, wherein the isolated nucleic acid molecule comprises a nucleic acid selected from the group consisting of SEQ ID NO: 2 and SEQ ID NO: 3.

8. A recombinant extrachromosomal vector, wherein the recombinant extrachromosomal vector comprises SEQ ID NO: 2, and encodes a subunit of the L-asparaginase II enzyme.

9. The recombinant extrachromosomal vector of claim 8 wherein the vector is a plasmid.

10. The recombinant extrachromosomal vector of claim 8 wherein the vector is plasmid pEN537.

11. An *Escherichia coli* host cell comprising the plasmid of claim 10, that is designated as EN538 and deposited as ATCC Number PTA 7490.

12. A method of producing a recombinant L-asparaginase II enzyme substantially free of other L-asparaginase II isomers, comprising culturing the host cell of claim 11, and isolating the produced L-asparaginase II enzyme.

13. An isolated DNA molecule encoding a subunit of L-asparaginase II enzyme that comprises SEQ ID NO: 2.

14. The recombinant extrachromosomal vector of claim 8 wherein SEQ ID NO: 2 is operatively connected to a suitable promoter.

15. The recombinant extrachromosomal vector of claim 14 wherein the promoter is selected from the group consisting of T7, araB, $P_R/P_L$, phoA, trc, and trp promoters.

* * * * *

SEQUENCE LISTING

```
<160> NUMBER OF SEQ ID NOS: 12

<210> SEQ ID NO 1
<211> LENGTH: 326
<212> TYPE: PRT
<213> ORGANISM: Escherichia coli

<400> SEQUENCE: 1

Leu Pro Asn Ile Thr Ile Leu Ala Thr Gly Gly Thr Ile Ala Gly Gly
1               5                   10                  15

Gly Asp Ser Ala Thr Lys Ser Asn Tyr Thr Ala Gly Lys Val Gly Val
            20                  25                  30

Glu Asn Leu Val Asn Ala Val Pro Gln Leu Lys Asp Ile Ala Asn Val
        35                  40                  45

Lys Gly Glu Gln Val Val Asn Ile Gly Ser Gln Asp Met Asn Asp Asp
    50                  55                  60

Val Trp Leu Thr Leu Ala Lys Lys Ile Asn Thr Asp Cys Asp Lys Thr
65                  70                  75                  80

Asp Gly Phe Val Ile Thr His Gly Thr Asp Thr Met Glu Glu Thr Ala
                85                  90                  95

Tyr Phe Leu Asp Leu Thr Val Lys Cys Asp Lys Pro Val Val Met Val
            100                 105                 110

Gly Ala Met Arg Pro Ser Thr Ser Met Ser Ala Asp Gly Pro Phe Asn
        115                 120                 125

Leu Tyr Asn Ala Val Val Thr Ala Ala Asp Lys Ala Ser Ala Asn Arg
    130                 135                 140
```

```
Gly Val Leu Val Val Met Asn Asp Thr Val Leu Asp Gly Arg Asp Val
145                 150                 155                 160

Thr Lys Thr Asn Thr Thr Asp Val Ala Thr Phe Lys Ser Val Asn Tyr
                165                 170                 175

Gly Pro Leu Gly Tyr Ile His Asn Gly Lys Ile Asp Tyr Gln Arg Thr
            180                 185                 190

Pro Ala Arg Lys His Thr Ser Asp Thr Pro Phe Asp Val Ser Lys Leu
        195                 200                 205

Asn Glu Leu Pro Lys Val Gly Ile Val Tyr Asn Tyr Ala Asn Ala Ser
    210                 215                 220

Asp Leu Pro Ala Lys Ala Leu Val Asp Ala Gly Tyr Asp Gly Ile Val
225                 230                 235                 240

Ser Ala Gly Val Gly Asn Gly Asn Leu Tyr Lys Thr Val Phe Asp Thr
                245                 250                 255

Leu Ala Thr Ala Ala Lys Asn Gly Thr Ala Val Val Arg Ser Ser Arg
            260                 265                 270

Val Pro Thr Gly Ala Thr Thr Gln Asp Ala Glu Val Asp Asp Ala Lys
        275                 280                 285

Tyr Gly Phe Val Ala Ser Gly Thr Leu Asn Pro Gln Lys Ala Arg Val
    290                 295                 300

Leu Leu Gln Leu Ala Leu Thr Gln Thr Lys Asp Pro Gln Gln Ile Gln
305                 310                 315                 320

Gln Ile Phe Asn Gln Tyr
                325

<210> SEQ ID NO 2
<211> LENGTH: 1530
<212> TYPE: DNA
<213> ORGANISM: Escherichia coli

<400> SEQUENCE: 2
aaatgggcgc gaaagcggtg ctgaaaagcg gcggtaaccc attacagaat gtgctgggaa        60
gcctgggaag cctgggggggg ctgcaatcct caatccaaac cgagtggaaa agcaggaaa       120 aagatttcca gcagtttggc aaagatgttt gtagccgcgt tgtgactctg aagatagcc       180 gcaaagccct ggtcgggaat ttaaaataat cctctatttt aagacggcat aatactttt       240 tatgccgttt aattcttcgt tttgttacct gcctctaact ttgtagatct ccaaaatata       300
ttcacgttgt aaattgttta acgtcaaatt tcccatacag agctaaggga taatgcgtag       360
cgttcacgta actggaggaa tgaaatggag ttttcaaaa agacggcact tgccgcactg       420
gttatgggtt ttagtggtgc agcattggca ttacccaata tcaccatttt agcaaccggc       480
gggaccattg ccggtggtgg tgactccgca accaaatcta actacacagc gggtaaagtt       540
ggcgtagaaa atctggttaa tgcggtgccg caactaaaag acattgcgaa cgttaaaggc       600
gagcaggtag tgaatatcgg ctcccaggac atgaacgatg atgtctggct gacactggcg       660
aaaaaaatta acaccgactg cgataagacc gacggcttcg tcattaccca cggtaccgac       720
acgatggaag aaactgctta cttcctcgac ctgacggtga atgcgacaa accggtggtg       780 atggtcggcg caatgcgtcc gtccacgtct atgagcgcag acggtccatt caacctgtat       840
aacgcggtag tgaccgcagc tgataaagcc tccgccaacc gtggcgtgct ggtagtgatg       900
aatgacaccg tgcttgatgg ccgtgacgtc accaaaacca acaccaccga cgtagcgacc       960
ttcaagtctg ttaactacgg tcctctgggt tacattcaca cggtaagat tgactaccag      1020
```

| | |
|---|---|
| cgtaccccgg cacgtaagca taccagcgac acgccattcg atgtctctaa gctgaatgaa | 1080 |
| ctgccgaaag tcggcattgt ttataactac gctaacgcat ccgatcttcc ggctaaagca | 1140 |
| ctggtagatg cgggctatga tggcatcgtt agcgctggtg tgggtaacgg caacctgtat | 1200 |
| aaaactgtgt tcgacacgct ggcgaccgcc gcgaaaaacg gtactgcagt cgtgcgttct | 1260 |
| tcccgcgtac cgacgggcgc taccactcag gatgccgaag tggatgatgc gaaatacggc | 1320 |
| ttcgtcgcct ctggcacgct gaacccgcaa aaagcgcgcg ttctgctgca actggctctg | 1380 |
| acgcaaacca agatccgca gcagatccag cagatcttca atcagtacta atcgcctcgc | 1440 |
| cccggtatcg tgccggggct ttttcacttc agactcacgt ccattgccaa ttttaattac | 1500 |
| cctaatgata atcaccggaa taaattattt | 1530 |

<210> SEQ ID NO 3
<211> LENGTH: 1044
<212> TYPE: DNA
<213> ORGANISM: Escherichia coli

<400> SEQUENCE: 3

| | |
|---|---|
| atggagtttt tcaaaaagac ggcacttgcc gcactggtta tgggttttag tggtgcagca | 60 |
| ttggcattac ccaatatcac cattttagca accggcggga ccattgccgg tggtggtgac | 120 |
| tccgcaacca aatctaacta cacagcgggt aaagttggcg tagaaaatct ggttaatgcg | 180 |
| gtgccgcaac tgaaggacat tgcgaacgtt aaaggcgagc aggtagtgaa tattggctcc | 240 |
| caggacatga acgatgatgt ctggctgaca ctggcgaaaa aaattaacac cgactgcgat | 300 |
| aaaactgacg gcttcgtcat taccccacggt accgacacga tggaagaaac cgcttacttc | 360 |
| ctcgacctga cggtgaaatg cgacaaaccg gtggtgatgg tcggtgcaat gcgtccgtcc | 420 |
| acgtctatga gcgcagacgg tccattcaac ctgtataacg cggtagtgac tgcagctgat | 480 |
| aaagcctccg ctaatcgtgg cgtactggta gtgatgaacg acaccgtgct tgatggccgt | 540 |
| gatgtcacca aaaccaacac caccgatgta gcgaccttca gtctgttaa ctacggtcct | 600 |
| ctgggttaca ttcacaacgg taagattgac taccaacgta ccccggcacg taagcacacc | 660 |
| agcgacacgc cgttcgatgt ctctaagctg aatgaactgc cgaaagtcgg cattgtttat | 720 |
| aactacgcta acgcatccga tcttccggct aaagcactgg tagatgcggg ctatgatggc | 780 |
| atcgttagcg ctggcgtggg taacggcaac ctgtataaaa ccgtatttga cacccttgca | 840 |
| accgctgcga aaacggcac tgcagtagtg cgttcttccc gcgtaccgac gggcgctacc | 900 |
| actcaggatg ccgaagtgga tgatgcgaaa tacggcttcg tcgcctctgg cacgttgaac | 960 |
| ccgcaaaaag cgcgcgttct gctgcaactg gctctgacgc aaactaaaga tccgcagcag | 1020 |
| atccagcaga tcttcaatca gtac | 1044 |

<210> SEQ ID NO 4
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 4

| | |
|---|---|
| tactgaattc atggagtttt tcaaaaagac ggca | 34 |

<210> SEQ ID NO 5
<211> LENGTH: 33
<212> TYPE: DNA
<213> ORGANISM: Artificial Sequence

```
<220> FEATURE:
<223> OTHER INFORMATION: oligonucleotide primer

<400> SEQUENCE: 5
acagtaagct tagtactgat tgaagatctg ctg                            33

<210> SEQ ID NO 6
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 6
caactttacc cgctgtgtag ttag                                      24

<210> SEQ ID NO 7
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 7
cagccagaca tcatcgttca tgtc                                      24

<210> SEQ ID NO 8
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 8
gtcgaacaca gttttataca ggttgc                                    26

<210> SEQ ID NO 9
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 9
ctgcagtacc gttttttcgcg gcgg                                     24

<210> SEQ ID NO 10
<211> LENGTH: 20
<212> TYPE: PRT
<213> ORGANISM: Escherichia coli

<400> SEQUENCE: 10

Leu Pro Asn Ile Thr Ile Leu Ala Thr Gly Gly Thr Ile Ala Gly Gly
1               5                   10                  15

Gly Asp Ser Ala
            20

<210> SEQ ID NO 11
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 11
```

-continued

```
gatccatatg gagtttttca aaaagacggc ac                                    32

<210> SEQ ID NO 12
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 12
gtacggatcc tcattagtac tgattgaaga tc                                    32
```